(12) United States Patent
Marlière

(10) Patent No.: US 10,947,569 B2
(45) Date of Patent: *Mar. 16, 2021

(54) RECOMBINANT MICROORGANISM FOR THE PRODUCTION OF USEFUL METABOLITES

(71) Applicant: Scientist of Fortune, S.A., Luxembourg (LU)

(72) Inventor: Philippe Marlière, Luxembourg (LU)

(73) Assignee: Scientist of Fortune, S.A., Luxembourg (LU)

( * ) Notice: Subject to any disclaimer, the term of this patent is extended or adjusted under 35 U.S.C. 154(b) by 11 days.

This patent is subject to a terminal disclaimer.

(21) Appl. No.: 16/280,304

(22) Filed: Feb. 20, 2019

(65) Prior Publication Data

US 2019/0169656 A1 Jun. 6, 2019

Related U.S. Application Data

(63) Continuation of application No. 14/956,658, filed on Dec. 2, 2015, now Pat. No. 10,240,169, which is a continuation of application No. 14/232,011, filed as application No. PCT/EP2012/063685 on Jul. 12, 2012, now Pat. No. 9,249,430.

(30) Foreign Application Priority Data

Jul. 12, 2011 (EP) .................................. 11173563

(51) Int. Cl.
| | |
|---|---|
| *C12P 7/28* | (2006.01) |
| *C12N 9/88* | (2006.01) |
| *C12N 9/16* | (2006.01) |
| *C12P 5/02* | (2006.01) |
| *C12N 15/63* | (2006.01) |
| *C12P 19/32* | (2006.01) |
| *C12P 17/18* | (2006.01) |

(52) U.S. Cl.
CPC ................ *C12P 7/28* (2013.01); *C12N 9/16* (2013.01); *C12N 9/88* (2013.01); *C12N 15/63* (2013.01); *C12P 5/026* (2013.01); *C12P 17/182* (2013.01); *C12P 19/32* (2013.01); *C12Y 301/03011* (2013.01); *C12Y 401/02009* (2013.01); *C12Y 401/02022* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 7,253,001 B2 | 8/2007 | Wahlbom et al. | |
| 7,371,558 B2 | 5/2008 | Cervin et al. | |
| 7,517,680 B2 | 4/2009 | Townsend et al. | |
| 7,785,858 B2 | 8/2010 | Kozlov et al. | |
| 7,977,084 B2 | 7/2011 | Sun et al. | |
| 8,241,877 B2 | 8/2012 | Burgard et al. | |
| 8,377,680 B2 | 2/2013 | Burk et al. | |
| 8,389,214 B2 | 3/2013 | Cervin et al. | |
| 8,865,439 B2 | 10/2014 | Burgard et al. | |
| 8,900,837 B2 | 12/2014 | Burgard et al. | |
| 8,993,305 B2 | 3/2015 | Beck et al. | |
| 9,246,430 B2 | 1/2016 | Chi | |
| 9,249,430 B2 | 2/2016 | Marliere | |
| 2004/0152174 A1 | 8/2004 | Cervin et al. | |
| 2005/0153411 A1 | 7/2005 | Wahlbom et al. | |
| 2006/0040365 A1 | 2/2006 | Kozlov et al. | |
| 2007/0161092 A1 | 7/2007 | Townsend et al. | |
| 2009/0142843 A1 | 6/2009 | Cervin et al. | |
| 2009/0155873 A1 | 6/2009 | Kashiyama et al. | |
| 2009/0275096 A1 | 11/2009 | Burgard et al. | |
| 2009/0275097 A1 | 11/2009 | Sun et al. | |
| 2010/0120105 A1 | 5/2010 | Anthony et al. | |
| 2010/0317069 A1 | 12/2010 | Burk et al. | |
| 2011/0144377 A1 | 6/2011 | Eliot et al. | |
| 2012/0040426 A1 | 2/2012 | Sun et al. | |
| 2012/0276605 A1 | 11/2012 | Burgard et al. | |
| 2012/0322078 A1 | 12/2012 | Mcbride et al. | |
| 2013/0089906 A1 | 4/2013 | Beck et al. | |
| 2013/0122553 A1 | 5/2013 | Maertens et al. | |
| 2013/0295616 A1 | 11/2013 | Muramatsu et al. | |
| 2014/0234923 A1 | 8/2014 | Yocum et al. | |

OTHER PUBLICATIONS

Arskold, et. al., "Phosphoketolase Pathway Dominates in Lactobacillus Reuteri ATCC 55730 Containing Dual Pathways for Glycolysis", Journal of Bacteriology, vol. 190, No. 1, Jan. 2008, pp. 206-212.
Barbe, et. al., "Unique Features Revealed by the Genome Sequence of *Acinetobecter* sp. AdP1, A Versatile and Naturally Transformation Competent Bacterium", Nucleic Acids Research, vol. 32, No. 19, 2004, pp. 5766-5779.
Bermejo, et. al., "Expression of Clostridium Acetobutylicum ATCC 824 Genes in *Escherichia coli* for Acetone Production and Acetate Detoxification", Applied and Environmental Microbiology, vol. 64, No. 3, Mar. 1998, pp. 1079-1085.
Chinen, et. al., "Innovative Metabolic Pathway Design for Efficient I-Glutamate Production by Supressing CO2 Emission", Journal of Bioscience and Bioengineering, vol. 103, No. 3, 2007, pp. 262-269.
Columbian Office Action dated Jun. 23, 2015.

(Continued)

*Primary Examiner* — Kagnew H Gebreyesus
(74) *Attorney, Agent, or Firm* — Michele M. Wales; Inhouse Patent Counsel, LLC

(57) ABSTRACT

Described are recombinant microorganisms characterized by having phosphoketolase activity, having a diminished or inactivated Embden-Meyerhof-Parnas pathway (EMPP) by inactivation of the gene(s) encoding phosphofructokinase or by reducing phosphofructokinase activity as compared to a non-modified microorganism and having a diminished or inactivated oxidative branch of the pentose phosphate pathway (PPP) by inactivation of the gene(s) encoding glucose-6-phosphate dehydrogenase or by reducing glucose-6-phosphate dehydrogenase activity as compared to a non-modified microorganism. These microorganisms can be used for the production of useful metabolites such as acetone, isobutene or propene.

19 Claims, 4 Drawing Sheets

Specification includes a Sequence Listing.

(56) References Cited

OTHER PUBLICATIONS

Danner, et. al., "Biotechnology for the Production of Commodity Chemicals From Biomass", Department for Environmental Technologies, vol. 38, Mar. 11, 1999, pp. 395-405.
Du, J., et. al., "Active-Site Remodeling in the Bifunctional Fructose-1,6-Bisphosphate Aldolase/Phosphatase", 2011, pp. 534-537.
Emmerling, et. al., "Glucose Catabolism of *Escherichia coli* Strains Wth Increased Activity and Altered Regulation of Key Glycolytic Enzymes", Metabolic Engineering, vol. 1., No. 1, 1999, pp. 127-177.
Ezeji, et. al., "Achievements and Perspectives to Overcome the Poor Solvent Resistance in Acetone and Butanol-Producing Microorganisms", Appl Microbial Biotechnol, vol. 85, 2010, pp. 1697-1712.
Fliege, et. al., "Establishment of an Alternative Phosphoketolase-Dependent Pathway for Fructose Catabolism in Ralstonia Eutropha H16", Applied Microbial and Cell Physiology, vol. 91, No. 3, 2011, pp. 769-776.
Flores, et. al., "Adaption for Fast Growth on Glucose by Differential Expression of Central Metabolism and Gal Regulon Genes in an *Escherichia coli* Strain Lacking the Phosphoenolpyruvate: Carbohydrate Phosphotransferase System", Metabolic Engineering, 2005, pp. 70-87.
Fushinobu, et. al., "Structural Basis for the Bifunctionality of Fructose-1,6-Bisphosphate Aldolase/Phosphatase", Nature, vol. 478, Oct. 27, 2011, pp. 538-541.
Gogerty, et. al., "Formation of Isobutene From 3-Hydroxy-3-Methylbutyrate by Diphosphomevalonate Decarboxylase", Applied and Environmental Microbiology, vol. 76, No. 24, Dec. 2010, pp. 8004-8010.
Hanai, et. al., "Engineered Synthetic Pathway for Isopropanol Production in *Escherichia coli*", Applied and Environmental Microbiology, vol. 73, No. 24, Dec. 2007, pp. 7814-7818.
Heinisch, J., "Construction and Physiological Characterization of Mutants Disrupted in the Phosphofrutokinase Genes of *Saccharomyces cerevisiae*", Current Genetics, vol. 11, No. 3, 1986, pp. 227-234.
Jeppsson, et. al., "Reduced Oxidative Pentose Phosphate Patheway Flux in Recombinant Xylose-Utilizing *Saccharomyces cerevisiae* Strains improves the Ethanol Yield From Xylose", Applied and Environmental Microbiology, vol. 68, No. 4, 2002, pp. 1604-1609.
Pearce, et. al., "Pyruvate Kinase (Pyk1) Levels Influence Both the Rate and Direction of Carbon Flux in Yeast Fermentative Conditions", Microbiology, vol. 147, 2001, pp. 391-401.
Posthuma, et. al., "Expression of the Xylulose 5-Phosphate Phoshoketolase Gene, xpkA, From Lactobacillus Pentosus MD363 Is Induced by Sugars That are Fermented Via the Phoshoketolase Pathway And is Repressed by Glucose Mediated by CcpA and the Mannose Phosphoenolpyruvate Phosphotransferase System", Applied and Environmental Microbiology, vol. 68, No. 2, 2002, pp. 813-837.
Rodicio, et. al., "Single Point Mutations in Either Gene Encoding the Subunits of the Heterooctameric Yeast Phosphofructokinase Abolish Allosteric Inhibition by ATP", The Journal of Biological Chemistry, vol. 275, No. 52, 2000, pp. 40952-40960.
Say, et. al., "Fructose 1,6-Bisphosphate Aldolase/Phosphatase May Be an Ancestral Gluconeogenic Enzyme", Nature, vol. 464, 2010, pp. 1077-1081.
Schwock, et. al., Interaction of 6-Phosphofructokinase With Cytosolic Proteins of *Saccharomyces cerevisiae*, vol. 21, No. 6, 2004, pp. 483-494.
Sonderegger, et. al., "Metabolic Engineering of a Phosphoketolase Pathway for Pentose Catabolism in *Saccharomyces cerevisiae*", Applied and Environmental Microbiology, vol. 70, No. 5, 2004, pp. 2892-2897.
Suo, et. al., "The Genomic Sequence of the Ethanologenic Bacterium Zymomonas Mobilis ZM4", Nature Biotechnology, vol. 23, No. 1, 2005, pp. 63-68.
Thorner, et. al., "Catalytic and Allosteric Properties of Glycol Kinase From *Escherichia coli*", the Journal of Biological Chemistry, vol. 248, No. 11, 1973, pp. 3922-3932.
Trinh, et. al., "Minimal *Escherichia coli* Cell for the Most Efficient Production of Ethanol From Hexoses and Pentoses", Applied and Environmental Microbiology, vol. 74, No. 12, Jun. 2008, pp. 3634-3643.
Veiga-Da-Cunha, et. al., "Pathway and Regulation of Erythritol Formation in Leuconostoc Oenos", Journal of Bacteriology, vol. 175, No. 13, Jul. 1993, pp. 3941-3948.

FIGURE 1

Scheme 1. Production of acetyl-CoA from glucose-6-phosphate via the phosphoketolase pathway, representative Case 1

1a.) 2 D-glucose-6-phosphate = 2 D-fructose-6-phosphate (EC 5.3.1.9)
1b.) D-fructose-6-phosphate + phosphate = acetyl phosphate + D-erythrose-4-phosphate + H$_2$O (EC 4.1.2.22)
1c.) D-erythrose-4-phosphate + D-fructose-6-phosphate = sedoheptulose-7-phosphate + D-glyceraldehyde-3-phosphate (EC 2.2.1.2)
1d.) Sedoheptulose-7-phosphate + D-glyceraldehyde-3-phosphate = D-ribose-5-phosphate + D-xylulose-5-phosphate (EC 2.2.1.1)
1e.) D-ribose-5-phosphate = D-ribulose-5-phosphate (EC 5.3.1.6)
1f.) D-ribulose-5-phosphate = D-xylulose-5-phosphate (EC 5.1.3.1)
1g.) 2 D-xylulose-5-phosphate + 2 phosphate = 2 acetyl phosphate + 2 D-glyceraldehyde-3-phosphate + 2 H$_2$O (EC 4.1.2.22 and/or EC 4.1.2.9)
1h.) 3 acetyl phosphate + 3 CoA = 3 acetyl-CoA + 3 phosphate (EC 2.3.1.8)

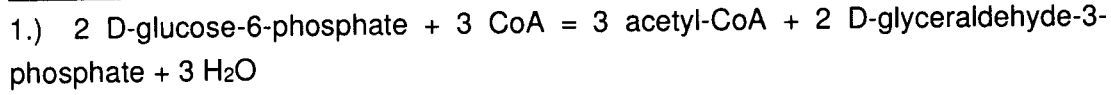

1.) 2 D-glucose-6-phosphate + 3 CoA = 3 acetyl-CoA + 2 D-glyceraldehyde-3-phosphate + 3 H$_2$O

Scheme 2. Production of Acetyl-CoA from glucose-6-phosphate via the phosphoketolase pathway, representative Case 2

2a.) 2 D-glucose-6-phosphate = 2 D-fructose-6-phosphate (EC 5.3.1.9)
2b.) D-fructose-6-phosphate + D-glyceraldehyde-3-phosphate = D-xylulose-5-phosphate + D-erythrose-4-phosphate (EC 2.2.1.1)
2c.) D-erythrose-4-phosphate + D-fructose-6-phosphate = sedoheptulose-7-phosphate + D-glyceraldehyde-3-phosphate (EC 2.2.1.2)
2d.) Sedoheptulose-7-phosphate + D-glyceraldehyde-3-phosphate = D-ribose-5-phosphate + D-xylulose-5-phosphate (EC 2.2.1.1)
2e.) D-ribose-5-phosphate = D-ribulose-5-phosphate (EC 5.3.1.6)
2f.) D-ribulose-5-phosphate = D-xylulose-5-phosphate (EC 5.1.3.1)
2g.) 3 D-xylulose-5-phosphate + 3 phosphate = 3 acetyl phosphate + 3 D-glyceraldehyde-3-phosphate + 3 H$_2$O (EC 4.1.2.9 and/or EC 4.1.2.22)

FIGURED 1 cont.

2h.)  3 acetyl phosphate + 3 CoA = 3 acetyl-CoA + 3 phosphate  (EC 2.3.1.8)

2.)  2 D-glucose-6-phosphate + 3 CoA = 3 acetyl-CoA + 2 D-glyceraldehyde-3-phosphate + 3 $H_2O$

TABLE OF RESULTS I

| | GBE1346 | GBE1347 | GBE1350 | GBE1351 |
|---|---|---|---|---|
| PEP dependent glucose uptake (*ptsHI*) | + | + | - | - |
| Heterologous phosphoketolase (*pkt*) | - | + | - | + |
| EMPP (*pfkAB*) | + | - | + | - |
| PPP (*zwf edd eda*) | + | - | + | - |
| Heterologous fructose bisphosphatase (*fbp*) | - | - | - | - |
| Heterologous acetone pathway (*thl ctfAB adc*) | + | + | + | + |
| [acetone]$_{produced}$/[glucose]$_{consumed}$ | 0.02 | >0.02 | 0.04 | 0.14 |

FIGURE 2

TABLE OF RESULTS II

| | GBE2264 | GBE2265 | GBE2268 | GBE2269 | GBE2268 | GBE2273 | GBE2272 | GBE2273 |
|---|---|---|---|---|---|---|---|---|
| PEP dependent glucose uptake (*ptsHI*) | + | + | - | - | - | - | - | - |
| Heterologous phosphoketolase (*pkt*) | - | + | - | + | - | + | + | + |
| EMPP (*pfkAB*) | + | - | + | - | + | - | - | - |
| PPP (*zwf*) | + | - | + | - | + | - | + | - |
| EDP (*edd eda*) | + | - | + | - | + | + | + | + |
| Heterologous acetone pathway (*thl ctfAB adc*) | + | + | + | + | + | + | + | + |
| [acetone]$_{produced\,(mM)}$/[glucose]$_{consumed\,(mM)}$ the reported ratio was the maximum observed | 0,03 | 0,21 | 0,01 | 0,22 | 0,01 | 0,51 | 0,05 | 0,51 |

FIGURE 3

RECOMBINANT MICROORGANISM FOR THE PRODUCTION OF USEFUL METABOLITES

This Application is a continuation of U.S. Ser. No. 14/956,658 filed on Dec. 2, 2015, which is a continuation of U.S. Ser. No. 14/232,011, filed on May 21, 2014, now issued as U.S. Pat. No. 9,249,430 on Feb. 2, 2016, which is a 371 National Phase Application of PCT/EP2012/063685 filed Jul. 12, 2012 and which claims priority to EP 111735635 filed on Jul. 12, 2011. The entire contents of these documents are hereby incorporated by reference in their entirety.

The present invention relates to a recombinant microorganism characterized by having phosphoketolase activity, having a diminished or inactivated Embden-Meyerhof-Parnas pathway (EMPP) by inactivation of the gene(s) encoding the phosphofructokinase or by reducing the phosphofructokinase activity as compared to a non-modified microorganism or not possessing phosphofructokinase activity and having a diminished or inactivated oxidative branch of the pentose phosphate pathway (PPP) by inactivation of the gene(s) encoding the glucose-6-phosphate dehydrogenase or by reducing the glucose-6-phosphate dehydrogenase activity as compared to a non-modified microorganism or not possessing glucose-6-phosphate dehydrogenase activity. Such a microorganism can be used for the production of useful metabolites such as acetone, isobutene or propene.

For the past several decades, practitioners of metabolic engineering have endeavoured to provide biological solutions for the production of chemicals, thus, providing alternatives to more traditional chemical processes. In general, biological solutions allow for the utilization of renewable feedstocks (e.g. sugars) and compete with existing petrochemical based processes. A multi-step, biological solution for the production of a chemical typically comprises a microorganism as the catalyst for the conversion of feedstock to a target molecule. A complete set of enzyme reactions for the production of a particular target molecule can be grouped into those belonging to central carbon pathways and those belonging to the product specific pathway. The reactions belonging to central carbon and product specific pathways are linked in that redox (typically, NAD(P)H) and energetic (typically, ATP) constraints of each and every enzyme reaction must be accounted for in an overall balance contributing to the competitiveness of the process. Historically, central carbon pathways of heterotrophs growing on sugars have been described as the Embden-Meyerhoff-Parnas pathway (EMPP), the pentose phosphate pathway (PPP), the Entner-Doudoroff pathway (EDP), and the phosphoketolase pathway (PKP) (see Gottschalk (1986), Bacterial Metabolism, 2$^{nd}$ Edition, Springer-Verlag, New York). Each central pathway or combinations of central pathways offer advantages and disadvantages with respect to a specific target molecule. In order to provide competitive bioprocesses, recombinant microorganisms with modifications involving the EMPP, PPP and EDP have been described (M. Emmerling et al., Metab. Eng. 1:117 (1999); L. O. Ingram et al., Appl. Environ. Microbiol. 53: 2420 (1987); C. T. Trinh et al., Appl. Environ. Microbiol. 74:3634 (2008)). More recently, recombinant microorganisms with modifications involving the PKP have been described (see Sonderegger et al. Appl. Environ. Microbiol. 70 (2004), 2892-2897, U.S. Pat. No. 7,253,001, Chinen et al. J. Biosci. Bioeng. 103 (2007), 262-269, U.S. Pat. No. 7,785,858; Fleige et al., Appl. Microbiol. Cell Physiol. 91 (2011), 769-776).

The EMPP converts 1 mol glucose to 2 mol pyruvate (PYR). When acetyl-CoA is desired, 1 mol PYR can be converted to 1 mol of acetyl-CoA with the concomitant generation of 1 mol $CO_2$ and 1 mol NADH. The sum of the reactions is given in Equation 1.

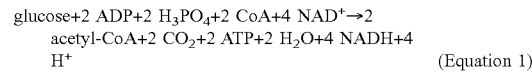

$$\text{glucose} + 2\ \text{ADP} + 2\ H_3PO_4 + 2\ \text{CoA} + 4\ \text{NAD}^+ \rightarrow 2\ \text{acetyl-CoA} + 2\ CO_2 + 2\ \text{ATP} + 2\ H_2O + 4\ \text{NADH} + 4\ H^+ \quad \text{(Equation 1)}$$

The PPP provides a means to convert 1 mol glucose to 1 mol $CO_2$ and 2 mol NADPH, with the concomitant generation of 0.67 mol fructose-6-phosphat (F6P) and 0.33 mol glyceraldehyde-3-phosphate (GAP). The F6P and GAP thus formed must be metabolized by other reaction pathways, e.g. by the EMPP. The EDP converts 1 mol glucose to 1 mol GAP and 1 mol PYR with the concomitant generation of 1 mol NADPH. As with the PPP, the GAP thus formed must be metabolized by other reaction pathways. The PKP provides a means to convert 1 mol glucose to 1 mol GAP and 1.5 mol acetyl phosphate (AcP). When acetyl-CoA is desired, 1 equivalent of AcP plus 1 equivalent coenzyme A (CoA) can be converted to 1 equivalent acetyl-CoA and 1 equivalent inorganic phosphate (Pi) by the action of phosphotransacetylase.

For specific target molecules derived from AcCoA moieties generated through the PKP and near redox neutrality to the AcCoA moieties, there exists a deficiency in the overall energy balance. The PKP (and, similarly, the PPP and EDP) does not generate ATP for the conversion of glucose to glucose-6-phosphate. In the case of phosphoenolpyruvate (PEP)-dependent glucose uptake, PEP must be generated by other means, e.g. through the EMPP. Recycling GAP through the PKP exacerbates the issue, particularly when the product specific pathway provides little ATP. Sonderegger (loc. cit.) and U.S. Pat. No. 7,253,001 disclose recombinant *Saccharomyces cerevisiae* strains comprising native or overexpressed phosphoketolase activity together with overexpressed phosphotransacetylase to increase the yield in the conversion of glucose/xylose mixtures to ethanol. These strains feature PEP-independent glucose uptake with both the EMPP and the PPP operative.

Chinen (loc. cit.) and U.S. Pat. No. 7,785,858 disclose a recombinant bacterium selected from the group consisting of the Enterobacteriaceae family, Coryneform bacterium, and *Bacillus* bacterium comprising increased phosphoketolase activity for the conversion of glucose to target molecules which are produced via the intermediate acetyl-CoA, including the group consisting of L-glutamic acid, L-glutamine, L-proline, L-arginine, L-leucine, L-cysteine, succinate and polyhydroxybutyrate. These strains feature PEP-dependent glucose uptake with the EMPP operative. Notably, the activity of phosphofructokinase in the bacterium of U.S. Pat. No. 7,785,858 is reduced compared to that of a wild-type or non-modified strain (see page 33).

Whether a particular microorganism utilizes PEP-independent glucose uptake or PEP-dependent glucose uptake impacts the overall energetic balance of a process. For example, *S. cerevisiae* strains naturally employ PEP-independent glucose uptake while *Escherichia coli* strains naturally employ PEP-dependent glucose uptake. *E. coli* strains have been disclosed where PEP-dependent glucose uptake has been replaced with PEP-independent glucose uptake. Flores et al. (Metabolic Engineering (2005) 7, 70-87) and U.S. Pat. No. 7,371,558. In particular, U.S. Pat. No. 7,371,558 discloses the glucose uptake modification to increase the yield in the conversion of glucose to 1,3-propanediol. The strains feature PEP-independent glucose uptake with both the EMPP and the PPP operative, notably with no phosphoketolase activity present.

There is a need to develop recombinant microorganisms, comprising central carbon and product specific pathways that maximize the conversion of feedstock to product by best accommodating the redox and energetic constraints of enzyme reactions. Applicants have addressed this need by providing the embodiments as defined in the claims.

Thus, the present invention relates to a recombinant microorganism characterized by:
a) having phosphoketolase activity;
b) (i) having a diminished or inactivated Embden-Meyerhof-Parnas pathway (EMPP) by inactivation of the gene(s) encoding phosphofructokinase or by reducing phosphofructokinase activity as compared to a non-modified microorganism; or
   (ii) not possessing phosphofructokinase activity and
c) (i) having a diminished or inactivated oxidative branch of the pentose phosphate pathway (PPP) by inactivation of the gene(s) encoding glucose-6-phosphate dehydrogenase or by reducing glucose-6-phosphate dehydrogenase activity as compared to a non-modified microorganism; or
   (ii) not possessing glucose-6-phosphate dehydrogenase activity.

The microorganism according to the present invention is characterised by having phosphoketolase activity, so as to increase the flux of acetyl-CoA produced. Usually, a microorganism converts glucose via the Embden-Meyerhof-Parnas pathway into pyruvate which can then be converted into acetyl-CoA by the enzyme pyruvate dehydrogenase. However, this conversion is accompanied by the release of $CO_2$ and, thus, one carbon atom is lost which might have been used in the production of useful metabolites. In order to increase the amount of acetyl-CoA in a microorganism it is therefore desirable that acetyl-CoA is formed via a different pathway to avoid the loss of carbon atoms. By using a microorganism having phosphoketolase activity, phosphate and fructose-6-phosphate are converted to erythrose-4-phosphate and acetylphosphate and the phosphotransacetylase further converts acetylphosphate into acetyl-CoA without loss of a carbon atom. Thus, in the end, the yield of acetyl-CoA can be increased by using a microorganism having phosphoketolase activity. Such a microorganism is capable of converting glucose into acetyl-CoA without loss of a carbon atom. Recombinant microorganisms in which a phosphoketolase is naturally or heterologously expressed are disclosed in U.S. Pat. Nos. 7,785,858 and 7,253,001.

The term "phosphoketolase activity" as used in the present invention means an enzymatic activity that is capable of converting D-xylulose-5-phosphate into D-glyceraldehyde-3-phosphate according to the following reaction:

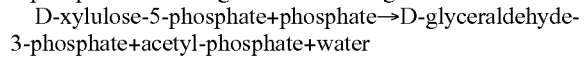
D-xylulose-5-phosphate+phosphate→D-glyceraldehyde-3-phosphate+acetyl-phosphate+water or that is capable to catalyze the above shown reaction and that is also able to convert D-fructose-6-phosphate to D-erythrose-4-phosphate according to the following reaction:

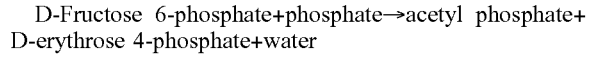
D-Fructose 6-phosphate+phosphate→acetyl phosphate+ D-erythrose 4-phosphate+water The former phosphoketolases are usually classified in EC 4.1.2.9 and the latter in EC 4.1.2.22. Both types of phosphoketolases can be employed in the scope of the present invention. FIG. 1 shows schemes for the overall reactions using the two options of the phosphoketolase as described herein.

This enzymatic activity can be measured by assays known in the art. An example for such an assay is given in the Example section below.

In the context of the present invention, a microorganism which has phosphoketolase activity can, e.g., be a microorganism which naturally has phosphoketolase activity or a microorganism that does not naturally have phosphoketolase activity and has been genetically modified to express a phosphoketolase or a microorganism which naturally has phosphoketolase activity and which has been genetically modified, e.g. transformed with a nucleic acid, e.g. a vector, encoding a phosphoketolase in order to increase the phosphoketolase activity in said microorganism.

Microorganisms that inherently, i.e. naturally, have phosphoketolase activity are known in the art and any of them can be used in the context of the present invention.

It is also possible in the context of the present invention that the microorganism is a microorganism which naturally does not have phosphoketolase activity but which is genetically modified so as to comprise a nucleotide sequence allowing the expression of a phosphoketolase. Similarly, the microorganism may also be a microorganism which naturally has phosphoketolase activity but which is genetically modified so as to enhance the phosphoketolase activity, e.g. by the introduction of an exogenous nucleotide sequence encoding a phosphoketolase.

The genetic modification of microorganisms to express an enzyme of interest will be described in detail below.

The phosphoketolase expressed in the microorganism according to the invention can be any phosphoketolase, in particular a phosphoketolase from prokaryotic or eukaryotic organisms. Prokaryotic phosphoketolases are described, e.g., from *Lactococcus lactis* and an example is given in the Example section.

In a preferred embodiment of the present invention the phosphoketolase is an enzyme comprising an amino acid sequence as encoded by SQ0005 shown in the Example section or a sequence which is at least n % identical to that amino acid sequence and having the activity of a phosphoketolase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99.

Preferably, the degree of identity is determined by comparing the respective sequence with the amino acid sequence of any one of the above-mentioned SEQ ID NOs. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of identity is calculated over the complete length of the sequence.

The phosphoketolase expressed in the microorganism according to the invention can be a naturally occurring phosphoketolase or it can be a phosphoketolase which is derived from a naturally occurring phosphoketolase, e.g. by the introduction of mutations or other alterations which, e.g., alter or improve the enzymatic activity, the stability, etc.

Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution". For example, for genetic modification in prokaryotic cells, a nucleic acid molecule encoding phosphoketolase can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be ligated by using adapters and linkers complementary to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting phosphoketolase variants are then tested for the desired activity, e.g., enzymatic activity, with an assay as described above and in particular for their increased enzyme activity.

As described above, the microorganism of the invention may be a microorganism which has been genetically modified by the introduction of a nucleic acid molecule encoding a phosphoketolase. Thus, in a preferred embodiment, the recombinant microorganism is a recombinant microorganism which has been genetically modified to have an increased phosphoketolase activity. This can be achieved e.g. by transforming the microorganism with a nucleic acid encoding a phosphoketolase. A detailed description of genetic modification of microorganisms will be given further below. Preferably, the nucleic acid molecule introduced into the microorganism is a nucleic acid molecule which is heterologous with respect to the microorganism, i.e. it does not naturally occur in said microorganism.

In the context of the present invention, an "increased activity" means that the expression and/or the activity of an enzyme, in particular of the phosphoketolase in the genetically modified microorganism is at least 10%, preferably at least 20%, more preferably at least 30% or 50%, even more preferably at least 70% or 80% and particularly preferred at least 90% or 100% higher than in the corresponding non-modified microorganism. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism.

The term "increased" expression/activity also covers the situation in which the corresponding non-modified microorganism does not express a corresponding enzyme, e.g. phosphoketolase, so that the corresponding expression/activity in the non-modified microorganism is zero.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

Methods for measuring the enzymatic activity of the phosphoketolase are known in the art and have already been described above.

The microorganism according to the present invention is further characterised by having a diminished or inactivated Embden-Meyerhof-Parnas pathway (EMPP) by inactivation of the gene(s) encoding a phosphofructokinase or by reducing the phosphofructokinase activity as compared to a non-modified microorganism or by not possessing phosphofructokinase activity. Thus, the microorganism is either a microorganism which naturally has an EMPP including phosphofructokinase activity but which has been modified, in particular genetically modified, so that the phosphofructokinase activity is either completely abolished or so that it is reduced compared to the corresponding non-modified microorganism, or the microorganism is a microorganism which naturally does not possess a phosphofructokinase activity.

As already mentioned above, when glucose is processed via the EMPP to acetyl-CoA, one carbon atom is lost by the release of $CO_2$ in the last step. By introducing the phosphoketolase, this loss can be avoided. Since fructose-6-phosphate is a substrate for the phosphoketolase, it is desirable that the pool of fructose-6-phosphate is kept at a high level in the microorganism in order to increase the yield in acetyl-CoA. Since fructose-6-phosphate is also a substrate for an enzyme of the Embden-Meyerhof-Parnas pathway, i.e. the phosphofructokinase, the recombinant microorganism of the present invention has a reduced phosphofructokinase activity as compared to a non-modified microorganism or the gene(s) encoding a phosphofructokinase has/have been inactivated. This ensures the flux of fructose-6-phosphate is directed to the phosphoketolase and to the production of acetyl-CoA without loss of $CO_2$ because fructose-6-phosphate or most of fructose-6-phosphate can no longer be processed via the Embden-Meyerhof-Parnas pathway. Recombinant microorganisms in which a phosphoketolase is naturally or heterologously expressed and which have reduced phosphofructokinase activity are disclosed in U.S. Pat. No. 7,785,858.

The "phosphofructokinase activity" means an enzymatic activity that converts ATP and fructose-6-phosphate to ADP and fructose-1,6-bisphosphate (EC 2.7.1.11). This enzymatic activity can be measured by assays known in the art as, for example, described by Kotlarz et al. (Methods Enzymol. (1982) 90, 60-70).

The term "a microorganism which is characterised by having a diminished or inactivated Embden-Meyerhof-Parnas pathway (EMPP) by inactivation of the gene(s) encoding a phosphofructokinase or by reducing the phosphofructokinase activity as compared to a non-modified microorganism" preferably refers to a microorganism in which the inactivation of the gene(s) encoding a phosphofructokinase or the reduction of the phosphofructokinase activity as compared to a non-modified microorganism is achieved by a genetic modification of the microorganism which leads to said inactivation or reduction.

In a preferred embodiment, the recombinant microorganism of the present invention is a recombinant microorganism that has an inactivated Embden-Meyerhof-Parnas pathway (EMPP) by inactivation of the gene(s) encoding a phosphofructokinase. The inactivation of the gene(s) encoding a phosphofructokinase in the context of the present invention means that the gene(s) coding for phosphofructokinase which are present in the microorganism is (are) inactivated so that they are no longer expressed and/or do not lead to the synthesis of functional phosphofructokinase. Inactivation can be achieved by many different ways known in the art. The inactivation can, e.g., be achieved by the disruption of the gene(s) encoding the phosphofructokinase or by clean deletion of said gene(s) through the introduction of a selection marker. Alternatively, the promoter of the gene(s) encoding the phosphofructokinase can be mutated in a way that the gene is no longer transcribed into mRNA. Other ways to inactivate the gene(s) encoding the phosphofructokinase known in the art are: to express a polynucleotide encoding RNA having a nucleotide sequence complementary to the transcript of the phosphofructokinase gene(s) so that the mRNA can no longer be translated into a protein, to express a polynucleotide encoding RNA that suppresses the expression of said gene(s) through RNAi effect; to express a polynucleotide encoding RNA having an activity of specifically cleaving a transcript of said gene(s); or to express a polynucleotide encoding RNA that suppresses expression of said gene(s) through co-suppression effect. These polynucleotides can be incorporated into a vector, which can be introduced into the microorganism by transformation to achieve the inactivation of the gene(s) encoding the phosphofructokinase.

The term "inactivation" in the context of the present invention preferably means complete inactivation, i.e. that the microorganism does not show phosphofructokinase activity. This means in particular that the microorganism does not show phosphofructokinase activity independent from the used growth conditions. Preferably, "inactivation" means that the gene(s) encoding phosphofructokinase which are present in the microorganism are genetically modified so as to prevent the expression of the enzyme. This can be achieved, e.g. by deletion of the gene or parts thereof wherein the deletion of parts thereof prevents expression of the enzyme, or by disruption of the gene either in the coding region or in the promoter region wherein the disruption has the effect that no protein is expressed or a dysfunctional protein is expressed.

In a preferred embodiment, the recombinant microorganism of the present invention is a recombinant microorganism that has a diminished Embden-Meyerhof-Parnas pathway (EMPP) by reducing the phosphofructokinase activity as compared to a non-modified microorganism. Preferably, this reduction is achieved by a genetic modification of the microorganism. This can be achieved e.g., by random mutagenesis or site-directed mutagenesis of the promoter and/or the enzyme and subsequent selection of promoters and/or enzymes having the desired properties or by complementary nucleotide sequences or RNAi effect as described above. A detailed description of genetic modification of microorganisms will be given further below.

In the context of the present invention, a "reduced activity" means that the expression and/or the activity of an enzyme, in particular of the phosphofructokinase, in the genetically modified microorganism is at least 10%, preferably at least 20%, more preferably at least 30% or 50%, even more preferably at least 70% or 80% and particularly preferred at least 90% or 100% lower than in the corresponding non-modified microorganism. Methods for measuring the level of expression of a given protein in a cell are well known to the person skilled in the art. Assays for measuring the reduced enzyme activity of a phosphofructokinase are known in the art.

In another embodiment the microorganism according to the present invention is a microorganism which does not possess a phosphofructokinase activity. This preferably means that such a microorganism naturally does not possess a phosphofructokinase activity. This means that such a microorganism does naturally not contain in its genome a nucleotide sequence encoding an enzyme with phosphofructokinase activity. Examples for such microorganisms are *Zymomonas mobilis* (J. S. Suo et al., Nat. Biotechnol. 23:63 (2005)) and *Ralstonia eutropha* (C. Fleige et al., Appl. Microb. Cell Physiol. 91:769 (2011)).

The microorganism according to the present invention is further characterised by having a diminished or inactivated oxidative branch of the pentose phosphate pathway (PPP) by inactivation of the gene(s) encoding a glucose-6-phosphate dehydrogenase or by reducing the glucose-6-phosphate dehydrogenase activity as compared to a non-modified microorganism or by not possessing glucose-6-phosphate dehydrogenase activity. Thus, the microorganism is either a microorganism which naturally has a PPP including glucose-6-phosphate dehydrogenase activity but which has been modified, in particular genetically modified, so that the glucose-6-phosphate dehydrogenase activity is either completely abolished or so that it is reduced compared to the corresponding non-modified microorganism, or the microorganism is a microorganism which naturally does not possess a glucose-6-phosphate dehydrogenase activity.

Diminishing or inactivating the oxidative branch of the pentose phosphate pathway further increases the yield in acetyl-CoA since glucose-6-phosphate will no longer be drawn through the pentose phosphate cycle. All or almost all glucose-6-phosphate in the microorganism will be converted into fructose-6-phosphate which will then be further converted into acetyl-CoA.

The "glucose-6-phosphate dehydrogenase activity" means an enzymatic activity that converts glucose-6-phosphate and $NADP^+$ to 6-phosphoglucono-$\delta$-lactone and NADPH (EC 1.1.1.49). This enzymatic activity can be measured by assays known in the art as, for example, described by Noltmann et al. (J. Biol. Chem. (1961) 236, 1225-1230).

The term "a microorganism which is characterised by having a diminished or inactivated oxidative branch of the pentose phosphate pathway (PPP) by inactivation of the gene(s) encoding a glucose-6-phosphate dehydrogenase or by reducing the glucose-6-phosphate dehydrogenase activity as compared to a non-modified microorganism" preferably refers to a microorganism in which the inactivation of the gene(s) encoding a glucose-6-phosphate dehydrogenase or the reduction of the glucose-6-phosphate dehydrogenase activity as compared to a non-modified microorganism is achieved by a genetic modification of the microorganism which leads to said inactivation or reduction.

In a preferred embodiment, the recombinant microorganism of the present invention is a recombinant microorganism that has an inactivated oxidative branch of the pentose phosphate pathway (PPP) by inactivation of the gene(s) encoding a glucose-6-phosphate dehydrogenase. The inactivation of the gene(s) encoding a glucose-6-phosphate dehydrogenase in the context of the present invention means that the gene(s) coding for glucose-6-phosphate dehydrogenase which is (are) present in the microorganism is (are) inactivated so that they are no longer expressed and/or do not lead to the synthesis of functional glucose-6-phosphate dehydrogenase. Inactivation can be achieved by many different ways known in the art. The inactivation can, e.g., be achieved by the disruption of the gene(s) encoding the glucose-6-phosphate dehydrogenase or by clean deletion of said gene(s) through the introduction of a selection marker. Alternatively, the promoter of the gene(s) encoding the glucose-6-phosphate dehydrogenase can be mutated in a way that the gene(s) is/are no longer transcribed into mRNA. Other ways to inactivate the gene(s) encoding the phosphofructokinase known in the art are: to express a polynucleotide encoding RNA having a nucleotide sequence complementary to the transcript of the glucose-6-phosphate dehydrogenase gene(s) so that the mRNA can no longer be translated into a protein, to express a polynucleotide encoding RNA that suppresses the expression of said gene(s) through RNAi effect; to express a polynucleotide encoding RNA having an activity of specifically cleaving a transcript of said gene(s); or to express a polynucleotide encoding RNA that suppresses expression of said gene(s) through co-suppression effect. These polynucleotides can be incorporated into a vector, which can be introduced into the microorganism by transformation to achieve the inactivation of the gene(s) encoding the glucose-6-phosphate dehydrogenase. The term "inactivation" in the context of the present invention preferably means complete inactivation, i.e. that the microorganism does not show glucose-6-phosphate dehydrogenase activity. This means in particular that the microorganism does not show glucose-6-phosphate dehydrogenase activity independent from the used growth conditions.

Preferably, "inactivation" means that the gene(s) encoding glucose-6-phosphate dehydrogenase which are present in the microorganism are genetically modified so as to prevent the expression of the enzyme. This can be achieved, e.g. by deletion of the gene or parts thereof wherein the deletion of parts thereof prevents expression of the enzyme, or by disruption of the gene either in the coding region or in the promoter region wherein the disruption has the effect that no protein is expressed or a dysfunctional protein is expressed.

In a preferred embodiment, the recombinant microorganism of the present invention is a recombinant microorganism that has a diminished oxidative branch of the pentose phosphate pathway (PPP) by reducing the glucose-6-phosphate dehydrogenase activity as compared to a non-modified microorganism. Preferably, this reduction is achieved by a genetic modification of the microorganism. This can be achieved e.g., by random mutagenesis or site-directed mutagenesis of the promoter and/or the enzyme and subsequent selection of promoters and/or enzymes having the desired properties or by complementary nucleotide sequences or RNAi effect as described above. A detailed description of genetic modification of microorganisms will be given further below.

In the context of the present invention, a "reduced activity" means that the expression and/or the activity of an enzyme, in particular of the glucose-6-phosphate dehydrogenase, in the genetically modified microorganism is at least 10%, preferably at least 20%, more preferably at least 30% or 50%, even more preferably at least 70% or 80% and particularly preferred at least 90% or 100% lower than in the corresponding non-modified microorganism. Methods for measuring the level of expression of a given protein in a cell are well known to the person skilled in the art. Assays for measuring the reduced enzyme activity of a glucose-6-phosphate dehydrogenase are known in the art.

In another embodiment the microorganism according to the present invention is a microorganism which does not possess a glucose-6-phosphate dehydrogenase activity. This preferably means that such a microorganism naturally does not possess a glucose-6-phosphate dehydrogenase activity. This means that such a microorganism does naturally not contain in its genome a nucleotide sequence encoding an enzyme with glucose-6-phosphate dehydrogenase activity. Examples for such microorganisms are *Acinetobacter baylyi* (Barbe et al., Nucl. Acids Res. 32 (2004), 5766-5779), archae of the hyperthermophilic phylum such as *Sulfolobus solfataricus* (Nunn et al., J. Biol. Chem. 285 (2010), 33701-33709), *Thermoproteus tenax*, *Thermoplasma acidophilum* and *Picrophilus torridus* (Reher and Schönheit, FEBS Lett. 580 (2006), 1198-1204).

In a further embodiment, the microorganism according to the present invention is further characterised by having fructose-1,6-bisphosphate phosphatase activity, preferably when grown on glucose. Fructose-1,6-bisphosphate phosphatase is an enzyme participating in the gluconeogenesis hydrolyzing fructose-1,6-bisphosphate into fructose-6-phosphate and free phosphate. However, in basically all organisms in the presence of glucose, fructose-1,6-bisphosphate phosphatase activity is repressed and glucose is processed through EMPP (glycolysis). The microorganism of the present invention, which has phosphoketolase activity and which does not possess phosphofructokinase activity or in which phosphofructokinase activity is reduced or whose gene encoding the phosphofructokinase is inactivated, the yield of acetyl-CoA by conversion of fructose-6-phosphate with the phosphoketolase (EC 4.1.2.9 or EC 4.1.2.22) can be enhanced by ensuring the presence of fructose-1,6-bisphosphate phosphatase activity, for example by derepression of the fructose-1,6-bisphosphate phosphatase in the presence of glucose. The presence of fructose-1,6-bisphosphate phosphatase activity results in the recycling of fructose-1,6-bisphosphate produced by fructose-1,6-bisphosphate aldolase into fructose-6-phosphate which can then again be converted via the phosphoketolase pathway to acetyl-CoA. Indeed, the product acetyl phosphate of phosphoketolase interconverts into acetyl-CoA through the action of the enzyme phosphate acetyltransferase EC 2.3.1.8. Thus, the recombinant microorganism of the present invention is capable of producing acetyl-CoA from glucose at a stoichiometry approaching 3:1. The sum of the reactions is given in equation 2:

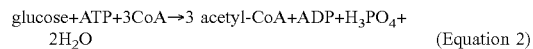

$$\text{glucose} + \text{ATP} + 3\text{CoA} \rightarrow 3 \text{ acetyl-CoA} + \text{ADP} + \text{H}_3\text{PO}_4 + 2\text{H}_2\text{O} \quad \text{(Equation 2)}$$

The term "fructose-1,6-bisphosphate phosphatase activity" means an enzymatic activity that converts fructose-1,6-bisphosphate and $H_2O$ to fructose-6-phosphate and phosphate (EC 3.1.3.11). This enzymatic activity can be measured by assays known in the art as, for example, described by Hines et al. (J. Biol. Chem. (2007) 282, 11696-11704). The terms "fructose-1,6-bisphosphate phosphatase activity" and "fructose-1,6-bisphosphate phosphatase" also cover enzymes which are bifunctional in the sense that they show a fructose-1-6-bisphosphate aldolase/phosphatase activity. Such bifunctional enzymes are expressed in most archaeal and deeply branching bacterial lineages and, in most cases, are heat-stable. Such enzymes are, for example, reported for *Thermococcus kodakaraensis*, *Sulfolobus tokodaii*, *Ignicoccus hospitalis*, *Cenarchaeum symbiosum*, *Sulfolobus solfataricas*, *Thermus thermophilus*, *Thermoproteus neutrophilus*, *Moorella thermoacetica* and many others (see, e.g., Say and Fuchs (Nature 464 (2010), 1077); Fushinobu et al. (Nature 478 (2011), 538; Du et al. (Nature 478 (2011), 534).

The term "fructose-1,6-bisphosphate phosphatase activity when grown on glucose" means that the microorganism expresses an enzyme with fructose-1,6-bisphosphate phosphatase activity when the microorganism is grown on glucose. "Grown on glucose" means that the microorganism is grown in a medium which contains inter alia glucose as carbon source. Preferably, this term means that the microorganism is grown in a medium containing glucose as sole carbon source.

In the context of the present invention, a microorganism which has fructose-1,6-bisphosphate phosphatase activity, in particular when grown on glucose, can, for example, be a microorganism which naturally has fructose-1,6-bisphosphate phosphatase activity, in particular when grown on glucose, or a microorganism that does not naturally have fructose-1,6-bisphosphate phosphatase activity, in particular when grown on glucose, and that has been genetically modified to express a fructose-1,6-bisphosphate phosphatase, in particular when grown on glucose. It may also be a microorganism which naturally has fructose-1,6-bisphosphate phosphatase activity, in particular when grown on glucose, and which has been genetically modified, e.g. transformed with a nucleic acid, e.g. a vector, encoding a fructose-1,6-bisphosphate phosphatase in order to increase the phosphoketolase activity in said microorganism.

Microorganisms that inherently, i.e. naturally, have fructose-1,6-bisphosphate phosphatase activity, in particular when grown on glucose, are known in the art and any of them can be used in the context of the present invention.

It is also possible in the context of the present invention that the microorganism is a microorganism which naturally does not have fructose-1,6-bisphosphate phosphatase activity, in particular when grown on glucose, but which is genetically modified so as to be able to express a fructose-1,6-bisphosphate phosphatase, in particular, when grown on glucose. This can be achieved, e.g., by mutating the promoter of the gene encoding the fructose-1,6-bisphosphate phosphatase in a way that the gene is no longer repressed when the microorganism is grown on glucose or the promoter can be replaced by another promoter e.g. a constitutive promoter which is not regulated when the microorganism is grown on glucose.

Similarly, the microorganism may also be a microorganism which naturally has fructose-1,6-bisphosphate phosphatase activity, in particular when grown on glucose, but which is genetically modified so as to enhance/increase the fructose-1,6-bisphosphate phosphatase activity, in particular when grown on glucose, e.g. by the introduction of an exogenous nucleotide sequence encoding a fructose-1,6-bisphosphate phosphatase.

The genetic modification of microorganisms to express an enzyme of interest will be described in detail below.

The fructose-1,6-bisphosphate phosphatase according to the invention can be a naturally occurring fructose-1,6-bisphosphate phosphatase or it can be a fructose-1,6-bisphosphate phosphatase which is derived from a naturally occurring fructose-1,6-bisphosphate phosphatase, e.g. by the introduction of mutations or other alterations which, e.g., alter or improve the enzymatic activity, the stability, etc. Methods for modifying and/or improving the desired enzymatic activities of proteins are well-known to the person skilled in the art and have been described above. The resulting fructose-1,6-bisphosphate phosphatase variants are then tested for their properties, e.g. enzymatic activity or regulation. Assays for measuring the enzyme activity of a fructose-1,6-bisphosphate phosphatase are known in the art.

In one embodiment the fructose-1,6-bisphosphate phosphatase is an enzyme which is not regulated by feed-back inhibition.

In a preferred embodiment, the recombinant microorganism has been genetically modified to have an increased fructose-1,6-bisphosphate phosphatase activity. This can be achieved e.g. by transforming the microorganism with a nucleic acid encoding a fructose-1,6-bisphosphate phosphatase. A detailed description of genetic modification of microorganisms will be given further below.

In the context of the present invention, an "increased activity" means that the expression and/or the activity of an enzyme, in particular of the fructose-1,6-bisphosphate phosphatase, in the genetically modified microorganism when grown on glucose is at least 10%, preferably at least 20%, more preferably at least 30% or 50%, even more preferably at least 70% or 80% and particularly preferred at least 90% or 100% higher than in the corresponding non-modified microorganism when grown on glucose. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism in particular when grown on glucose.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

Methods for measuring the enzymatic activity of the fructose-1,6-bisphosphate are known in the art.

In another embodiment, the microorganism according to the present invention is further characterised in that the EMPP is further diminished or inactivated by inactivation of the gene(s) encoding the glyceraldehyde 3-phosphate dehydrogenase or by reducing the glyceraldehyde 3-phosphate dehydrogenase activity as compared to a non-modified microorganism. Further diminishing the EMPP at a step further downstream by diminishing or inactivating the glyceraldehyde 3-phosphate dehydrogenase ensures that none or almost none glyceraldehyde 3-phosphate that may be produced in the microorganism will be processed via the glycolysis to acetyl-CoA whereby one carbon atom would be lost by the release of $CO_2$ in the last step catalysed by the pyruvate dehydrogenase. Therefore, blocking the EMPP by diminishing or inactivating the glyceraldehyde 3-phosphate dehydrogenase activity further ensures that the overall flux is directed towards the phosphoketolase.

The "glyceraldehyde 3-phosphate dehydrogenase activity" means an enzymatic activity that converts glyceraldehyde 3-phosphate, phosphate and $NAD^+$ to 3-phospho-D-glyceroyl phosphate and $NADH+H^+$ (EC 1.2.1.12). This activity can be measured by assays known in the art as, for example, described by D'Alessio et al. (J. Biol. Chem. (1971) 246, 4326-4333).

The term "a microorganism which is characterised by having a further diminished or inactivated Embden-Meyerhof-Parnas pathway (EMPP) by inactivation of the gene(s) encoding a glyceraldehyde 3-phosphate dehydrogenase or by reducing the glyceraldehyde 3-phosphate dehydrogenase activity as compared to a non-modified microorganism" preferably refers to a microorganism in which the inactivation of the gene(s) encoding a glyceraldehyde 3-phosphate dehydrogenase or the reduction of the glyceraldehyde 3-phosphate dehydrogenase activity as compared to a non-modified microorganism is achieved by a genetic modification of the microorganism which leads to said inactivation or reduction.

In a preferred embodiment, the recombinant microorganism of the present invention is a recombinant microorganism in which the EMPP is further diminished or inactivated by inactivation of the gene(s) encoding the glyceraldehyde 3-phosphate dehydrogenase or by reducing the glyceraldehyde 3-phosphate dehydrogenase activity as compared to a non-modified microorganism. The inactivation of the gene(s) encoding a glyceraldehyde 3-phosphate dehydrogenase in the context of the present invention means that the gene(s) coding for glyceraldehyde 3-phosphate dehydrogenase which is (are) present in the microorganism is (are) inactivated so that they are no longer expressed and/or do not lead to the synthesis of functional glyceraldehyde 3-phosphate dehydrogenase. Inactivation can be achieved by many different ways known in the art. The inactivation can, e.g., be achieved by the disruption of the gene(s) encoding the glyceraldehyde 3-phosphate dehydrogenase or by clean deletion of said gene(s) through the introduction of a selection marker. Alternatively, the promoter of the gene encoding the glyceraldehyde 3-phosphate dehydrogenase can be mutated in a way that the gene(s) is/are no longer transcribed into mRNA. Other ways to inactivate the gene(s) encoding the glyceraldehyde 3-phosphate dehydrogenase known in the art are: to express a polynucleotide encoding RNA having a nucleotide sequence complementary to the transcript of the glyceraldehyde 3-phosphate dehydrogenase gene(s) so that the mRNA can no longer be translated into a protein, to express a polynucleotide encoding RNA that suppresses the expression of said gene(s) through RNAi effect; to express a polynucleotide encoding RNA having an activity of specifically cleaving a transcript of said gene(s); or to express a polynucleotide encoding RNA that suppresses expression of said gene(s) through co-suppression effect. These polynucleotides can be incorporated into a vector, which can be introduced into the microorganism by transformation to achieve the inactivation of the gene(s) encoding the glyceraldehyde 3-phosphate dehydrogenase.

The term "inactivation" in the context of the present invention preferably means complete inactivation, i.e. that the microorganism does not show glyceraldehyde 3-phosphate dehydrogenase activity. This means in particular that the microorganism does not show glyceraldehyde 3-phosphate dehydrogenase activity independent from the used growth conditions.

Preferably, "inactivation" means that the gene(s) encoding glyceraldehyde 3-phosphate dehydrogenase which are present in the microorganism are genetically modified so as to prevent the expression of the enzyme. This can be achieved, e.g. by deletion of the gene or parts thereof wherein the deletion of parts thereof prevents expression of the enzyme, or by disruption of the gene either in the coding region or in the promoter region wherein the disruption has the effect that no protein is expressed or a dysfunctional protein is expressed.

In a preferred embodiment, the recombinant microorganism of the present invention is a recombinant microorganism that has a diminished EMPP by reducing the glyceraldehyde 3-phosphate dehydrogenase activity as compared to a non-modified microorganism. Preferably, this reduction is achieved by a genetic modification of the microorganism. This can be achieved e.g., by random mutagenesis or site-directed mutagenesis of the promoter and/or the enzyme and subsequent selection of promoters and/or enzymes having the desired properties or by complementary nucleotide sequences or RNAi effect as described above. A detailed description of genetic modification of microorganisms will be given further below.

In the context of the present invention, a "reduced activity" means that the expression and/or the activity of an enzyme, in particular of the glyceraldehyde 3-phosphate dehydrogenase, in the genetically modified microorganism is at least 10%, preferably at least 20%, more preferably at least 30% or 50%, even more preferably at least 70% or 80% and particularly preferred at least 90% or 100% lower than in the corresponding non-modified microorganism. Methods for measuring the level of expression of a given protein in a cell are well known to the person skilled in the art. Assays for measuring the reduced enzyme activity of a glyceraldehyde 3-phosphate dehydrogenase are known in the art.

The term "microorganism" in the context of the present invention refers to bacteria, as well as to fungi, such as yeasts, and also to algae and archaea. In one preferred embodiment, the microorganism is a bacterium. In principle any bacterium can be used. Preferred bacteria to be employed in the process according to the invention are bacteria of the genus *Bacillus, Clostridium, Corynebacterium, Pseudomonas, Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum*.

In another preferred embodiment the microorganism is a fungus, more preferably a fungus of the genus *Saccharomyces, Schizosaccharomyces, Aspergillus, Trichoderma, Kluyveromyces* or *Pichia* and even more preferably of the species *Saccharomyces cerevisiae, Schizosaccharomyces pombe, Aspergillus niger, Trichoderma reesei, Kluyveromyces marxianus, Kluyveromyces lactis, Pichia pastoris, Pichia torula* or *Pichia utilis*.

In a more preferred embodiment, where the recombinant microorganism is a bacterium, the gene(s) encoding the PEP-dependent PTS transporter have been inactivated. In the context of the present invention, inactivation means that the gene(s) coding for PEP-dependent PTS transporter which is (are) present in the microorganism is (are) inactivated so that they are no longer expressed and/or do not lead to the synthesis of functional PEP-dependent PTS transporter. The inactivation of the gene(s) encoding the PEP-dependent PTS transporter should be such that the bacteria are no longer capable of transporting glucose via the PEP-dependent PTS transporter.

PEP-dependent PTS transporter (e.g. from *E. coli, B. subtilis*) are known in the art. An example for inactivation of the PEP-dependent PTS transporter is shown in the Example section below.

Inactivation can be achieved by many different ways known in the art. The inactivation can, e.g., be achieved by the disruption of the gene(s) encoding the PEP-dependent PTS transporter or by clean deletion of said gene(s) through the introduction of a selection marker. Alternatively, the promoter of the gene(s) encoding the PEP-dependent PTS transporter can be mutated in a way that the gene(s) is (are) no longer transcribed into mRNA. Other ways to inactivate the gene(s) encoding the PEP-dependent PTS transporter known in the art are: to express a polynucleotide encoding RNA having a nucleotide sequence complementary to the transcript of the PEP-dependent PTS transporter gene(s) so that the mRNA can no longer be translated into a protein, to express a polynucleotide encoding RNA that suppresses the expression of said gene(s) through RNAi effect; to express a polynucleotide encoding RNA having an activity of specifically cleaving a transcript of said gene(s); or to express a polynucleotide encoding RNA that suppresses expression of said gene(s) through co-suppression effect. These polynucleotides can be incorporated into a vector, which can be introduced into the microorganism by transformation to achieve the inactivation of the gene(s) encoding the PEP-dependent PTS transporter.

The term "recombinant" means that the microorganism of the present invention is genetically modified so as to contain a nucleic acid molecule encoding an enzyme as defined above as compared to a wild-type or non-modified microorganism or so that a gene encoding an enzyme as defined above has been deleted as compared to a wild-type or non-modified microorganism.

A nucleic acid molecule encoding an enzyme as defined above can be used alone or as part of a vector.

The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Alternatively, mutants can be prepared the catalytic activity of which is abolished without losing substrate binding activity.

Furthermore, the introduction of mutations into the polynucleotides encoding an enzyme as defined above allows the gene expression rate and/or the activity of the enzymes encoded by said polynucleotides to be reduced or increased.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Thus, in accordance with the present invention a recombinant microorganism can be produced by genetically modifying fungi or bacteria comprising introducing the above-described polynucleotides, nucleic acid molecules or vectors into a fungus or bacterium.

The invention relates to recombinant microorganisms, in particular bacteria and fungi, genetically modified with the above-described polynucleotides, nucleic acid molecules or vectors or obtainable by the above-mentioned method for producing genetically modified bacteria or fungi, and to cells derived from such transformed bacteria or fungi and containing a polynucleotide, nucleic acid molecule or vector as defined above. In a preferred embodiment the host cell is genetically modified in such a way that it contains the polynucleotide stably integrated into the genome.

The polynucleotide is expressed so as to lead to the production of a polypeptide having any of the activities described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

In another aspect of the present invention, the recombinant microorganism is further characterized in that it is capable of converting acetyl-CoA into acetone. Methods for providing such a recombinant microorganism are for instance disclosed in EP 2 295 593. The term "which is capable of converting acetyl-CoA into acetone" in the context of the present invention means that the organism/microorganism has the capacity to produce acetone within the cell due to the presence of enzymes providing enzymatic activities allowing the production of acetone from acetyl-CoA.

Acetone is produced by certain microorganisms, such as *Clostridium acetobutylicum, Clostridium beijerinckii, Clostridium cellulolyticum, Bacillus polymyxa* and *Pseudomonas putida*. The synthesis of acetone is best characterized in *Clostridium acetobutylicum*. It starts out with a reaction (reaction step 1) in which two molecules of acetyl-CoA are condensed into acetoacetyl-CoA. This reaction is catalyzed by acetyl-CoA acetyltransferase (EC 2.3.1.9). Acetoacetyl-CoA is then converted into acetoacetate by a reaction with acetic acid or butyric acid resulting also in the production of acetyl-CoA or butyryl-CoA (reaction step 2). This reaction is catalyzed e.g. by acetoacetylCoA transferase (EC 2.8.3.8). AcetoacetylCoA transferase is known from various organisms, e.g. from *E. coli* in which it is encoded by the atoAD gene or from *Clostridium acetobutylicum* in which it is encoded by the ctfAB gene. However, also other enzymes can catalyze this reaction, e.g. 3-oxoacid CoA transferase (EC 2.8.3.5) or succinate CoA ligase (EC 6.2.1.5).

Finally, acetoacetate is converted into acetone by a decarboxylation step (reaction step 3) catalyzed by acetoacetate decarboxylase (EC 4.1.1.4).

The above described reaction steps 1 and 2 and the enzymes catalyzing them are not characteristic for the acetone synthesis and can be found in various organism. In contrast, reaction step 3 which is catalyzed by acetoacetate decarboxylase (EC 4.1.1.4) is only found in those organisms which are capable of producing acetone.

In a preferred embodiment the recombinant microorganism of the present invention is a microorganism, which naturally has the capacity to produce acetone. Thus, preferably the microorganism belongs to the genus *Clostridium, Bacillus* or *Pseudomonas*, more preferably to the species *Clostridium acetobutylicum, Clostridium beijerinckii, Clostridium cellulolyticum, Bacillus polymyxa* or *Pseudomonas putida*.

In another preferred embodiment, the recombinant microorganism of the present invention is a microorganism, derived from an organism/microorganism which naturally does not produce acetone but which has been genetically modified so as to produce acetone, i.e. by introducing the gene(s) necessary for allowing the production of acetone in the microorganism. In principle any microorganism can be genetically modified in this way. The enzymes responsible for the synthesis of acetone have been described above. Genes encoding corresponding enzymes are known in the art and can be used to genetically modify a given microorganism so as to produce acetone. As described above, the reaction steps 1 and 2 of the acetone synthesis occur naturally in most organisms. However, reaction step 3 is characteristic and crucial for acetone synthesis. Thus, in a preferred embodiment, a genetically modified microorganism derived from a microorganism which naturally does not produce acetone is modified so as to contain a nucleotide sequence encoding an enzyme catalyzing the conversion of acetoacetate into acetone by decarboxylation, e.g. an acetoacetate decarboxylase (EC 4.1.1.4). Nucleotide sequences from several organisms encoding this enzyme are known in the art, e.g. the adc gene from *Clostridium acetobutylicum* (Uniprot accession numbers P23670 and P23673), *Clostridium beijerinckii* (*Clostridium* MP; Q9RPK1), *Clostridium pasteurianum* (Uniprot accession number P81336), *Bradyrhizobium* sp. (strain BTAi1/ATCC BAA-1182; Uniprot accession number A5EBU7), *Burkholderia mallei* (ATCC 10399 A9LBS0), *Burkholderia mallei* (Uniprot accession number A3MAE3), *Burkholderia mallei* FMH A5XJB2, *Burkholderia cenocepacia* (Uniprot accession number A0B471), *Burkholderia ambifaria* (Uniprot accession number Q0b5P1), *Burkholderia phytofirmans* (Uniprot accession number B2T319), *Burkholderia* spec. (Uniprot accession number Q38ZU0), *Clostridium botulinum* (Uniprot accession number B2TLN8), *Ralstonia pickettii* (Uniprot accession number B2UIG7), *Streptomyces nogalater* (Uniprot accession number Q9EYI7), *Streptomyces avermitilis* (Uniprot accession number Q82NF4), *Legionella pneumophila* (Uniprot accession number Q5ZXQ9), *Lactobacillus salivarius* (Uniprot accession number Q1WVG5), *Rhodococcus* spec. (Uniprot accession number QOS7W4), *Lactobacillus plantarum* (Uniprot accession number 0890G0), *Rhizobium leguminosarum* (Uniprot accession number Q1M911), *Lactobacillus casei* (Uniprot accession number 003B66), *Francisella tularensis* (Uniprot accession number QOBLC9), *Saccharopolyspora erythreae*

(Uniprot accession number A4FKR9), Korarchaeum cryptofilum (Uniprot accession number B1L3N6), *Bacillus amyloliquefaciens* (Uniprot accession number A7Z8K8), *Cochliobolus heterostrophus* (Uniprot accession number Q8NJQ3), *Sulfolobus islandicus* (Uniprot accession number C3ML22) and *Francisella tularensis* subsp. *holarctica* (strain OSU18).

More preferably, the microorganism is genetically modified so as to be transformed with a nucleic acid molecule encoding an enzyme capable of catalyzing the above mentioned reaction step 2 of the acetone synthesis, i.e. the conversion of acetoacetyl CoA into acetoacetate.

Even more preferably, the microorganism is genetically modified so as to be transformed with a nucleic acid molecule encoding an enzyme capable of catalyzing the above mentioned reaction step 1 of the acetone synthesis, i.e. the condensation of two molecules of acetyl CoA into acetoacetyl CoA.

In a particularly preferred embodiment the microorganism is genetically modified so as to be transformed with a nucleic acid molecule encoding an enzyme capable of catalyzing the above mentioned reaction step 1 of the acetone synthesis and with a nucleic acid molecule encoding an enzyme capable of catalyzing the above mentioned reaction step 2 of the acetone synthesis or with a nucleic acid molecule encoding an enzyme capable of catalyzing the above mentioned reaction step 1 of the acetone synthesis and with a nucleic acid molecule encoding an enzyme capable of catalyzing the above mentioned reaction step 3 of the acetone synthesis or with a nucleic acid molecule encoding an enzyme capable of catalyzing the above mentioned reaction step 2 of the acetone synthesis and with a nucleic acid molecule encoding an enzyme capable of catalyzing the above mentioned reaction step 3 of the acetone synthesis or with a nucleic acid molecule encoding an enzyme capable of catalyzing the above mentioned reaction step 1 of the acetone synthesis and with a nucleic acid molecule encoding an enzyme capable of catalyzing the above mentioned reaction step 2 of the acetone synthesis and with a nucleic acid molecule encoding an enzyme capable of catalyzing the above mentioned reaction step 3 of the acetone synthesis.

Methods for preparing the above mentioned genetically modified microorganisms are well known in the art. Thus, generally, the microorganism is transformed with a DNA construct allowing expression of the respective enzyme in the microorganism. Such a construct normally comprises the coding sequence in question linked to regulatory sequences allowing transcription and translation in the respective host cell, e.g. a promoter and/enhancer and/or transcription terminator and/or ribosome binding sites etc. The prior art already describes microorganisms which have been genetically modified so as to be able to produce acetone. In particular genes from, e.g., *Clostridium acetobutylicum* have been introduced into *E. coli* thereby allowing the synthesis of acetone in *E. coli*, a bacterium which naturally does not produce acetone (Bermejo et al., Appl. Environ. Microbiol. 64 (1998); 1079-1085; Hanai et al., Appl. Environ. Microbiol. 73 (2007), 7814-7818). In particular Hanai et al. (loc. cit.) shows that it is sufficient to introduce a nucleic acid sequence encoding an acetoacetate decarboxylase (such as that from *Clostridium acetobutylicum*) in order to achieve acetone production in *E. coli* indicating that the endogenous enzymes in *E. coli* catalyzing the above-mentioned reaction steps 1 and 2 (i.e. the expression products of the *E. coli* atoB and atoAD genes) are sufficient to provide substrate for the acetone production.

In another aspect of the present invention, the recombinant microorganism is further characterized in that it is capable of converting acetyl-CoA into acetone and converting acetone into isobutene. Methods for providing such a recombinant microorganism are for instance disclosed in EP-A 2 295 593 (EP 09 17 0312), WO 2010/001078 and EP 10 18 8001.

In another aspect of the present invention, the recombinant microorganism is characterized in that it is capable of converting acetyl-CoA into acetone and converting acetone into propene. Methods for providing such a recombinant microorganism are for instance disclosed in Hanai et al., Appl. Environ. Microbiol. 73 (2007), 7814-7818.

One skilled in the art would recognize that further genetic modifications to the microorganisms of the present invention could lead to improvements in the efficacy by which the microorganisms of the present invention convert feedstock to product. For example, natural microorganisms commonly produce products such as formate, acetate, lactate, succinate, ethanol, glycerol, 2,3-butanediol, methylglyoxal and hydrogen; all of which would be deleterious to the production of, e.g., acetone, isobutene or propene from sugars. Elimination or substantial reduction of such unwanted by-products may be achieved by elimination or reduction of key enzymes activities leading their production. Such activities include, but are not limited to, the group consisting of:

acetyl-CoA+formate=CoA+pyruvate (for example, catalyzed by formate C-acetyltransferase, also known as pyruvate formate-lyase (EC 2.3.1.54); for *E. coli*—pfl B, NCBI-GeneID: 945514);

ATP+acetate=ADP+acetyl phosphate (for example, catalyzed by acetate kinase (EC 2.7.2.1); for *E. coli*—ackA, NCBI-GeneID: 946775);

(R)-lactate+NAD$^+$=pyruvate+NADH+H$^+$ (for example, catalyzed by L-lactate dehydrogenase (EC 1.1.1.28); for *E. coli*—ldhA, NCBI-GeneID: 946315);

phosphate+oxaloacetate=phosphoenolpyruvate+HCO$_3^-$ (for example, catalyzed by phosphoenolpyruvate carboxylase (EC 4.1.1.31); for *E. coli*—ppc, NCBI-GeneID: 948457);

ATP+oxaloacetate=ADP+phosphoenolpyruvate+CO$_2$ (for example, catalyzed by phosphoenolpyruvate carboxykinase (ATP) (EC 4.1.1.49); for *E. coli*—pck, NCBI-GeneID: 945667);

succinate+acceptor=fumarate+reduced acceptor (for example, catalyzed by succinate dehydrogenase (EC 1.3.99.1); for *E. coli*—comprising frdA and frdB, NCBI-GeneID: 948667 and 948666, respectively);

a 2-oxo carboxylate (e.g. pyruvate)=an aldehyde (e.g. acetaldehyde+CO$_2$ (for example, catalyzed by pyruvate decarboxylase (EC 4.1.1.1));

acetaldehyde+CoA+NAD$^+$=acetyl-CoA+NADH+H$^+$ (for example, catalyzed by acetaldehyde dehydrogenase (acetylating) (EC 1.2.1.10); for *E. coli*—adhE, NCBI-GeneID: 945837);

sn-glycerol 3-phosphate+NAD(P)$^+$=glycerone phosphate+NAD(P)H+H$^+$ (for example, catalyzed by glycerol-3-phosphate dehydrogenase [NAD(P)+] (EC 1.1.1.94); for *E. coli*—gpsA, NCBI-GeneID: 948125);

2 pyruvate=2-acetolactate+CO$_2$ (for example, catalyzed by acetolactate synthase (EC 2.2.1.6); for *E. coli*—ilvH and ilvI, NCBI-GeneID: 947267 and 948793, respectively);

glycerone phosphate=methylglyoxal+phosphate (for example, catalyzed by methylglyoxal synthase (EC 4.2.3.3); for *E. coli*—mgsA, NCBI-GeneID: 945574); and formate+H⁺=CO₂+H₂ (for example, catalyzed by formate hydrogenlyase (EC 1.2.1.2 together with EC 1.12.1.2); for *E. coli*—fdhF (EC 1.2.1.2), NCBI-GeneID: 948584).

Thus, in a preferred embodiment, the microorganism according to the invention is characterized in that one or more of the above listed enzyme activities are eliminated or reduced.

One skilled in the art would further recognize that genetic modifications to regulatory elements in the microorganisms of the present invention could lead to improvements in the efficacy by which the microorganisms of the present invention convert feedstock to product. Within *E. coli*, such genetic modifications include, but are not limited to, the group consisting of:

deleting the fnr gene (NCBI-GeneID: 945908), a global regulator of anaerobic growth; and
deleting the rpoS gene (NCBI-GeneID: 947210), a RNA polymerase, sigma S (sigma 38) factor.

Thus, in another preferred embodiment the microorganism according to the invention shows at least one of these deletions.

A further aspect of the present invention is the use of the recombinant microorganism of the present invention for the conversion of glucose into acetyl-CoA. Acetyl CoA (also known as acetyl Coenzyme A) in chemical structure is the thioester between coenzyme A (a thiol) and acetic acid and is an important precursor molecule for the production of useful metabolites. Acetyl-CoA can then be further converted by the recombinant microorganism into useful metabolites such as L-glutamic acid, L-glutamine, L-proline, L-arginine, L-leucine, succinate and polyhydroxybutyrate.

Another aspect of the present invention is the use of the recombinant microorganism of the present invention that is capable of converting acetyl-CoA into acetone for the conversion of glucose into acetone.

A further aspect of the present invention is the use of the recombinant microorganism of the present invention that is capable of converting acetyl-CoA into acetone and acetone into isobutene for the conversion of glucose into isobutene.

Again a further aspect of the present invention is the use of the recombinant microorganism of the present invention that is capable of converting acetyl-CoA into acetone and acetone into propene for the conversion of glucose into propene.

Accordingly, the present invention also relates to a method for the production of acetone and/or isobutene and/or propene from glucose in which the above-mentioned recombinant microorganism is cultivated under conditions allowing for the production of acetone and/or isobutene and/or propene and in which the acetone and/or isobutene and/or propene is isolated. The microorganisms are cultivated under suitable culture conditions allowing the occurrence of the enzymatic reaction(s). The specific culture conditions depend on the specific microorganism employed but are well known to the person skilled in the art. The culture conditions are generally chosen in such a manner that they allow the expression of the genes encoding the enzymes for the respective reactions. Various methods are known to the person skilled in the art in order to improve and fine-tune the expression of certain genes at certain stages of the culture such as induction of gene expression by chemical inducers or by a temperature shift.

In another preferred embodiment the method according to the invention furthermore comprises the step of collecting gaseous products, in particular isobutene or propene, degassing out of the reaction, i.e. recovering the products which degas, e.g., out of the culture. Thus in a preferred embodiment, the method is carried out in the presence of a system for collecting isobutene or propene under gaseous form during the reaction.

As a matter of fact, short alkenes such as isobutene and propene adopt the gaseous state at room temperature and atmospheric pressure. The method according to the invention therefore does not require extraction of the product from the liquid culture medium, a step which is always very costly when performed at industrial scale. The evacuation and storage of the gaseous hydrocarbons and their possible subsequent physical separation and chemical conversion can be performed according to any method known to one of skill in the art.

The present invention is further described by reference to the following non-limiting figures and examples.

FIG. 1 shows two schemes for the production of acetyl-CoA from glucose-6-phosphate via the phosphoketolase pathway using either one or both phosphoketolase activities EC 4.1.2.9 and EC 4.1.2.22.

FIG. 2 shows the ratio [acetone]produced (mM)/[glucose] consumed (mM) was higher for the strain GBE1351 than for the strain GBE1350.

FIG. 3 shows the ratio [acetone] produced (mM)/[glucose] consumed (mM) was higher for the strain GBE2273 than for the strain GBE2272.

EXAMPLES

General Methods and Materials

Procedure for ligations and transformations are well known in the art. Techniques suitable for use in the following examples may be found in Sambrook J., et al., Molecular Cloning: A Laboratory Manual, 2nd Edition, Cold Spring Harbor, N.Y., 1989, and Sambrook J., supra.

Materials and methods suitable for the maintenance and growth of bacterial cultures are well known in the art. Techniques suitable for use in the following examples may be found in Manual of Methods for General Bacteriology (Philipp Gerhardt, R. G. E. Murray, Ralph N. Costilow, Eugene W. Nester, Willis A. Wood, Noel R. Krieg and G. Briggs Philips, eds).

All reagents and materials used for the growth and maintenance of bacterial cells were obtained from Sigma-Aldrich Company (St. Louis, Mo.) unless otherwise specified.

TABLE 1

Plasmids used and constructed

| Plasmid Name | Description |
|---|---|
| pKD46 | Datsenko KA. And Wanner BL., Proceedings of the National Academy of Sciences, 2000, Vol. 97, No. 12, pp. 6640-6645 |
| pCP20 | Datsenko KA. And Wanner BL., Proceedings of the National Academy of Sciences, 2000, Vol. 97, No. 12, pp. 6640-6645 |
| pGBE0687 | Plasmid pGBE0687 presents a resistance gene to apramycin placed under the control of its own promoter |
| pGBE0688 | Plasmid pGBE0688 presents a resistance gene to spectinomycin placed under the control of its own promoter |
| pGBE0421 | Plasmid from GeneArt ® (Invitrogen) that encodes for *L. lactis* phosphoketolase |

TABLE 1-continued

Plasmids used and constructed

| Plasmid Name | Description |
| --- | --- |
| pGBE0123 | A modified version of the plasmid pUC18 (New England Biolabs) which contains a modified Multiple Cloning Site (MCS) |
| pGBE0457 | Plasmid that allows expression of the *L. lactis* phosphoketolase |
| pGBE0689 | pBluescript II phagemids, Agilent Technologies |
| pGBE0690 | ctfA and ctfB genes from *Clostridium acetobutylicum* cloned into pGBE0689 |
| pGBE0691 | adc gene from *Clostridium acetobutylicum* cloned into pGBE0690 |
| pGBE0051 | pUC19, New England Biolabs |
| pGBE0692 | ctfA, ctfB and adc genes from *Clostridium acetobutylicum* cloned into pGBE0051 |
| pGBE0693 | thl gene from from *Clostridium acetobutylicum* cloned into pGBE0692 |
| pGBE0124 | A modified version of the plasmid pSU18 (Borja Bartolomé, Yolanda Jubete, Eduardo Martinez and Fernando de la Cruz, Gene, 1991, Vol. 102, Issue 1, pp. 75-78) |
| pGBE0096 | thl, ctfA, ctfB and adc genes from *Clostridium acetobutylicum* cloned into pGBE0124 |
| pGBE0928 | Plasmid that allows expression of the *L. lactis* phosphoketolase |
| pGBE1020 | Plasmid that allows expression of the *L. lactis* phosphoketolase and acetone production |
| pGBE1021 | Plasmid that allows acetone production |

TABLE 2

Strains used and constructed. FRT:FLP recognition target

| Strain name | Genotype | Strain of origin | Construction |
| --- | --- | --- | --- |
| GBE0129 | F-lambda-ilvG-rfb-50 rph-1 | | *Escherichia coli* K12 wild-type MG1655 |
| GBE0170 | pKD46 | GBE0129 | Transformation of the strain GBE0129 with the pKD46 plasmid |
| GBE0329 | pGBE0096 | GBE0129 | Transformation of the strain GBE0129 with the pGBE0096 plasmid |
| GBE0901 | ΔptsHI::FRT | GBE0129 | |
| GBE0902 | ΔptsHI::FRT pKD46 | GBE0901 | Transformation of the strain GBE0901 with the pKD46 plasmid |
| GBE0903 | ΔptsHI::FRT Δzwf_edd_eda::aad+ | GBE0902 | |
| GBE0929 | ΔptsHI::FRT | GBE0901 | Selection of the strain GBE0901 on MS medium with glucose as the source of carbon. |
| GBE1000 | ΔptsHI::FRT Δzwf_edd_eda::aad+ | GBE0903. | Selection of the strain GBE0903 on MS medium with glucose as the source of carbon. |
| GBE1001 | ΔptsHI::FRT Δzwf_edd_eda::aad+ pKD46 | GBE1000 | Transformation of the strain GBE1000 with the pKD46 plasmid |
| GBE1005_pKD46 | ΔptsHI::FRT Δzwf_edd_eda::aad+ ΔpfkA::aac+ | GBE1001 | |
| GBE1005 | ΔptsHI::FRT Δzwf_edd_eda::aad+ ΔpfkA::aac+ | GBE1005_pKD46. | The loss of the pKD46 plasmid has been verified. |
| GBE1005_p | ΔptsHI::FRT Δzwf_edd_eda::aad+ ΔpfkA::aac+ pCP20 | GBE1005 | Transformation of the strain GBE1005 with the pCP20 plasmid |
| GBE1006 | ΔptsHI::FRT Δzwf_edd_eda::FRT ΔpfkA::FRT | GBE1005_p | The loss of the pCP20 plasmid has been verified. |
| GBE1010 | ΔptsHI::FRT Δzwf_edd_eda::FRT ΔpfkA::FRT pKD46 | GBE1006 | Transformation of the strain GBE1006 with the pKD46 plasmid |
| GBE1014_pKD46 | ΔptsHI::FRT Δzwf-edd_eda::FRT ΔpfkA::FRT ΔpfkB::aad+ | GBE1010 | |
| GBE1014 | ΔptsHI::FRT Δzwf_edd_eda::FRT ΔpfkA::FRT ΔpfkB:: aad+ | GBE1014_pKD46. | The loss of the pKD46 plasmid has been verified. |
| GBE1283 | ΔptsHI::FRT | GBE0929 | Successive cultures of the GBE0929 in MS medium with glucose as the source of carbon. |
| GBE1284 | ΔptsHI::FRT pKD46 | GBE1283 | Transformation of the strain GBE1283 with the pKD46 plasmid |

TABLE 2-continued

Strains used and constructed.
FRT:FLP recognition target

| Strain name | Genotype | Strain of origin | Construction |
|---|---|---|---|
| GBE1287 | ΔptsHI::FRT Δzwf_edd_eda::aad+ | GBE1284 | |
| GBE1337 | ΔptsHI::FRT Δzwf_edd_eda::aad+ pKD46 | GBE1287 | Transformation of the strain GBE1287 with the pKD46 plasmid |
| GBE1339 | Δzwf_edd_eda::aac+ | GBE0170 | |
| GBE1340 | Δzwf_edd_eda::aac+ pKD46 | GBE1339 | Transformation of the strain GBE1339 with the pKD46 plasmid |
| GBE1341_pKD46 | Δzwf_edd_eda::aac+ ΔpfkA:: aad+ | GBE1340 | |
| GBE1341 | Δzwf_edd_eda::aac+ ΔpfkA:: aad+ | GBE1341_pKD46 | The loss of the pKD46 plasmid has been verified. |
| GBE1341_p | Δzwf_edd_eda::aac+ ΔpfkA:: aad+ pCP20 | GBE1341 | Transformation of the strain GBE1341 with the pCP20 plasmid |
| GBE1342 | Δzwf_edd_eda::FRT ΔpfkA::FRT | GBE1341_p | The loss of the pCP20 plasmid has been verified. |
| GBE1343 | Δzwf_edd_eda::FRT ΔpfkA::FRT pKD46 | GBE1342 | Transformation of the strain GBE1342 with the pKD46 plasmid |
| GBE1344_pKD46 | Δzwf_edd_eda::FRT ΔpfkA::FRT ΔpfkB:: aad+ | GBE1343 | |
| GBE1344 | Δzwf_edd_eda::FRT ΔpfkA::FRT ΔpfkB:: aad+ | GBE1344_pKD46 | The loss of the pKD46 plasmid has been verified. |
| GBE1345 | Δzwf_edd_eda::FRT ΔpfkA::FRT ΔpfkB:: aad+ pGBE457 pGBE0096 | GBE1344 | Transformation of the strain GBE1344 with both pGBE96 and pGB457 plasmids |
| GBE1346 | pGBE0096 | GBE0329 | Adaptation of the strain GBE0329 to the MS medium + glucose (2 g/L) + Chloramphenicol (25 ug/ml) |
| GBE1347 | Δzwf_edd_eda::FRT ΔpfkA::FRT ΔpfkB:: aad+ pGBE457 pGBE96 | GBE1345 | Adaptation of the strain GBE1345 to the MS medium + glucose (2 g/L) + Chloramphenicol (25 ug/ml) |
| GBE1348 | ΔptsHI::FRT pGB96 | GBE0929 | Transformation of the strain GBE0929 with both pGBE96 and pGB457 plasmids |
| GBE1349 | ΔptsHI::FRT Δzwf_edd_eda::FRT ΔpfkA::FRT ΔpfkB:: aad+ pGBE457 pGBE0096 | GBE1014 | Transformation of the strain GBE1014 with both pGBE96 and pGB457 plasmids |
| GBE1350 | ΔptsHI::FRT pGB96 | GBE1348 | Adaptation of the strain GBE1348 to the MS medium + glucose (2 g/L) + Chloramphenicol (25 ug/ml) |
| GBE1351 | ΔptsHI::FRT Δzwf_edd_eda::FRT ΔpfkA::FRT ΔpfkB:: aad+ pGBE457 pGBE0096 | GBE1349 | Adaptation of the strain GBE1349 to the MS medium + glucose (2 g/L) + Chloramphenicol (25 ug/ml) |
| GBE1353_pKD46 | ΔptsHI::FRT Δzwf_edd_eda::aad+ ΔpfkA::aac+ | GBE1337 | |
| GBE1353 | ΔptsHI::FRT Δzwf_edd_eda::aad+ ΔpfkA::aac+ | GBE1353_pKD46 | The loss of the pKD46 plasmid has been verified. |
| GBE1353_p | ΔptsHI::FRT Δzwf_edd_eda::aad+ ΔpfkA:: aac+ pCP20 | GBE1353 | Transformation of the strain GBE1353 with the pCP20 plasmid |
| GBE1368 | ΔptsHI::FRT Δzwf_edd_eda:: FRT ΔpfkA:: FRT | GBE1353_p | The loss of the pCP20 plasmid has been verified. |
| GBE1371 | ΔptsHI::FRT Δzwf_edd_eda:: FRT ΔpfkA:: FRT pKD46 | GBE1368 | Transformation of the strain GBE1368 with the pKD46 plasmid |
| GBE1420_pKD46 | ΔptsHI::FRT Δzwf_edd_eda:: FRT ΔpfkA:: FRT ΔpfkB:: aad+ | GBE1371 | |
| GBE1420 | ΔptsHI::FRT Δzwf_edd_eda:: FRT ΔpfkA:: FRT ΔpfkB:: aad+ | GBE1420_pKD46 | The loss of the pKD46 plasmid has been verified. |

TABLE 2-continued

Strains used and constructed.
FRT:FLP recognition target

| Strain name | Genotype | Strain of origin | Construction |
|---|---|---|---|
| GBE1433 | ΔptsHI::FRT Δzwf:: aad+ | GBE1284 | |
| GBE1436 | ΔptsHI::FRT Δzwf:: aad+ pKD46 | GBE1433 | Transformation of the strain GBE1433 with the pKD46 plasmid |
| GBE1441_pKD46 | ΔptsHI::FRT Δzwf:: aad+ ΔpfkA:: aac+ | GBE1436 | |
| GBE1441 | ΔptsHI::FRT Δzwf:: aad+ ΔpfkA:: aac+ | GBE1441_pKD46 | The loss of the pKD46 plasmid has been verified. |
| GBE1441_p | ΔptsHI::FRT Δzwf:: aad+ ΔpfkA:: aac+ pCP20 | GBE1441 | Transformation of the strain GBE1441 with the pCP20 plasmid |
| GBE1448 | ΔptsHI::FRT Δzwf:: FRT ΔpfkA:: FRT | GBE1441_p | The loss of the pCP20 plasmid has been verified. |
| GBE1449 | ΔptsHI::FRT Δzwf:: FRT ΔpfkA:: FRT pKD46 | GBE1448 | Transformation of the strain GBE1448 with the pKD46 plasmid |
| GBE1518_pKD46 | ΔptsHI::FRT Δzwf:: FRT ΔpfkA:: FRT ΔpfkB:: aad+ | GBE1449 | |
| GBE1518 | ΔptsHI::FRT Δzwf:: FRT ΔpfkA:: FRT ΔpfkB:: aad+ | GBE1518_pKD46 | The loss of the pKD46 plasmid has been verified. |
| GBE2252_pKD46 | ΔptsHI::FRT ΔpfkA:: aad+ | GBE1284 | |
| GBE2252 | ΔptsHI::FRT ΔpfkA:: aad+ | GBE2252_pKD46 | The loss of the pKD46 plasmid has been verified. |
| GBE2253 | ΔptsHI::FRT ΔpfkA:: aad+ pKD46 | GBE2252 | Transformation of the strain GBE2252 with the pKD46 plasmid |
| GBE2256_pKD46 | ΔptsHI::FRT ΔpfkA:: aad+ ΔpfkB:: aac+ | GBE2253 | |
| GBE2256 | ΔptsHI::FRT ΔpfkA:: aad+ ΔpfkB:: aac+ | GBE2256_pKD46 | The loss of the pKD46 plasmid has been verified. |
| GBE2262 | F-lambda-ilvG-rfb-50 rph-1 pGB1021 | GBE0129 | Transformation of the strain GBE0129 with pGB1021 plasmid |
| GBE2263 | Δzwf_edd_eda::FRT ΔpfkA::FRT ΔpfkB:: aad+ pGB1020 | GBE1344 | Transformation of the strain GBE1344 with pGB1020 plasmid |
| GBE2264 | F-lambda-ilvG-rfb-50 rph-1 pGB1021 | GBE2262 | Adaptation of the strain GBE2262 to the MS medium + glucose (2 g/L) + ampicilline (100 ug/ml). |
| GBE2265 | Δzwf_edd_eda::FRT ΔpfkA::FRT ΔpfkB:: aad+ pGB1020 | GBE2263 | Adaptation of the strain GBE2263 to the MS medium + glucose (2 g/L) + ampicilline (100 ug/ml). |
| GBE2266 | ΔptsHI::FRT pGB1021 | GBE1283 | Transformation of the strain GBE1283 with pGB1021 plasmid |
| GBE2267 | ΔptsHI::FRT Δzwf_edd_eda:: FRT ΔpfkA:: FRT ΔpfkB:: aad+ pGB1020 | GBE1420 | Transformation of the strain GBE1420 with pGB1020 plasmid |
| GBE2268 | ΔptsHI::FRT pGB1021 | GBE2266 | Adaptation of the strain GBE2266 to the MS medium + glucose (2 g/L) + ampicilline (100 ug/ml). |
| GBE2269 | ΔptsHI::FRT Δzwf_edd_eda:: FRT ΔpfkA:: FRT ΔpfkB:: aad+ pGB1020 | GBE2267 | Adaptation of the strain GBE2267 to the MS medium + glucose (2 g/L) + ampicilline (100 ug/ml). |
| GBE2270 | ΔptsHI::FRT ΔpfkA:: aad+ ΔpfkB:: aac+ pGB1020 | GBE2256 | Transformation of the strain GBE2256 with pGB1020 plasmid |
| GBE2271 | ΔptsHI::FRT Δzwf:: FRT ΔpfkA:: FRT ΔpfkB:: aad+ pGB1020 | GBE1518 | Transformation of the strain GBE1518 with pGB1020 plasmid |
| GBE2272 | ΔptsHI::FRT ΔpfkA:: aad+ ΔpfkB:: aac+ pGB1020 | GBE2270 | Adaptation of the strain GBE2270 to the MS medium + glucose (2 g/L) + ampicilline (100 ug/ml). |

TABLE 2-continued

Strains used and constructed.
FRT:FLP recognition target

| Strain name | Genotype | Strain of origin | Construction |
|---|---|---|---|
| GBE2273 | ΔptsHI::FRT Δzwf:: FRT ΔpfkA:: FRT ΔpfkB:: aad+ pGB1020 | GBE2271 | Adaptation of the strain GBE2271 to the MS medium + glucose (2 g/L) + ampicilline (100 ug/ml). |

TABLE 3

Sequences of bacterial chromosomal regions, genes used, plasmids regions.

| Name | Nucleotide sequence | Description | SEQ ID NO |
|---|---|---|---|
| nucleotide sequence from strain GBE0901, from base pairs 2531736 to 2531870 | Aggctagactttagttccacaacactaaacctataagttggggaaat acagtgtaggctggagctgcttc<u>gaagttcctatactttctagagaata</u> <u>ggaactt</u>cggaataggaactaaggaggatattcatatg | FRT region is underlined | SQ 0001 |
| Spectinomycin resistance cassette | agagcggccgccaccgcggg<u>aagttcctatactttctagagaatag</u> <u>gaactt</u>cagctgatagaaacagaagccactggagcacctcaaaa acaccatcatacactaaatcagtaagttggcagcatcacccgacgc actttgcgccgaataaatacctgtgacggaagatcacttcgcagaat aaataaatcctggtgtccctgttgataccgggaagccctgggccaac ttttggcgaaaatgagacgttgatcggcacgtaagaggttccaacttt caccataatgaaataagatcactaccgggcgtatttttttgagttatcga gattttcaggagctaaggaagctacatatgagtgaaaaagtgcccg ccgagatttcggtgcaactatcacaagcactcaacgtcatcgggcg ccacttggagtcgacgttgctggccgtgcatttgtacggctccgcact ggatggcggattgaaaccgtacagtgatattgatttgctggtgactgt agctgcaccgctcaatgatgccgtgcggcaagccctgctcgtcgat ctcttggaggtttcagcttcccctggccaaaacaaggcactccgcgc cttggaagtgaccatcgtcgtgcacagtgacatcgtaccttggcgtta tccggccaggcgggaactgcagttcggagagtggcagcgcaaag acatccttgcgggcatcttcgagcccgccacaaccgattctgacttg gcgattctgctaacaaaggcaaagcaacatagcgtcgtcttggcag gttcagcagcgaaggatctcttcagctcagtcccagaaagcgatcta ttcaaggcactggccgatactctgaagctatggaactcgccgccag attgggcggcgatgagcggaatgtagtgcttactttgtctcgtatctg gtacaccgcagcaaccggcaagatcgcgccaaaggatgttgctgc cacttgggcaatggcacgcttgccagctcaacatcagcccatcctgt tgaatgccaagcgggcttatcttgggcaagaagaagattatttgccc gctcgtgcggatcaggtggcggcgctcattaaattcgtgaagtatga agcagttaaactgcttggtgccagccaataa<u>gaagttcctatactttct</u> <u>agagaataggaactt</u>cgcatgcacgcagcatatgc | FRT regions are underlined | SQ 0002 |
| Apramycin resistance cassette | agagcggccgccaccgcggg<u>aagttcctatactttctagagaatag</u> <u>gaactt</u>cgggttcatgtgcagctccatcagcaaaaggggatgataa gtttatcaccaccgactatttgcaacagtgccgttgatcgtgctatgat gactgatgtcatcagccggtggagtgcaatgtcgtgcaatacgaatgg cgaaaagccgagctcatcggtcagcttctcaaccttggggttaccc cggcggtgtgctgctggtccacagctccttccgtagcgtccggcccct cgaagatgggccacttggactgatcgaggccctgcgtgctgcgctg ggtccgggagggacgctcgtcatgccctcgtggtcaggtctggacg acgagccgttcgatcctgccacgtcgcccgttacaccggaccttgga gttgtctctgacacattctggcgcctgccaaatgtaaagcgcagcgc ccatccatttgcctttgcggcagcggggccacaggcagagcagatc atctctgatccattgccctgccacctcactcgcctgcaagcccggtc gcccgtgtccatgaactcgatgggcaggtacttctcctcggcgtggg acacgatgccaacacgacgctgcatcttgccgagttgatggcaaag gttccctatggggtgccgagacactgcaccattcttcaggatggcaa gttggtacgcgtcgattatctcgagaatgaccactgctgtgagcgctt gccttggcggacaggtggctcaaggagaagagccttcagaagga aggtccagtcggtcatgccttttgctcggttgatccgctcccgcgacatt gtggcgacagccctgggtcaactgggccgagatccgttgatcttcct gcatccgccagaggcgggatgcgaagaatgcgatgccgctcgcc agtcgattggctgagctcatgagcggagaacgagatgacgttgga ggggcaaggtcgcgctgattgctggggcaacacgtggagcggatc | FRT regions are underlined | SQ 0003 |

TABLE 3-continued

Sequences of bacterial chromosomal regions, genes used, plasmids regions.

| Name | Nucleotide sequence | Description | SEQ ID NO |
|---|---|---|---|
| | ggggattgtctttcttcagctcgctgatgatatgctgacgctcaatgcc gaagttcctatactttctagagaataggaacttcgcatgcacgcagc atatgc | | |
| MCS of the pGB0123 plasmid | <u>AAGCTT</u>GCGGCCGCGGGGTTAATTAACCTCCT TAGTTTAAACCTAGGCATGCCTCTAGAGGATC CCCGGGTACCGAGCTCGAAttaCCTGCAG<u>GAAT TC</u> | The restriction sites for HindIII and EcoRI are underlined. | SQ 0004 |
| Optimized *Lactococcus lactis* phosphoketolase gene flanked by PacI and NotI restriction sites | <u>TTAATTAA</u>TGCATCATCACCACCATCACATGAC CGAATATAACAGCGAAGCCTATCTGAAAAACT GGATAAATGGTGGCGTGCAGCAACCTATCTGG GTGCAGGTATGATTTTTCTGAAAGAAATCCGC TGTTTAGCGTTACCGGCACCCCGATTAAAGCA GAAAATCTGAAAGCCAATCCGATTGGTCATTG GGCACCGTTAGCGGTCAGACCTTTCTGTATG CACATGCAAATCGCCTGATTAACAAATATAACC AGAAAATGTTTTATATGGGTGGTCCGGGTCAT GGTGGTCAGGCAATGGTTGTTCCGAGCTATCT GGATGGTAGCTATACCGAAGCATATCCGGAAA TTACCCAGGATCTGGAAGGTATGAGCCGTCTG TTTAAACGTTTTAGCTTTCCGGGTGGTATTGGT AGCCACATGACCGCACAGACACCGGGTAGCC TGCATGAAGGTGGTGAACTGGGTTATGTTCTG AGCCATGCAACCGGTGCAATTCTGGATCAGCC GGAACAAATTGCATTTGCAGTTGTTGGTGATG GTGAAGCAGAAACCGGTCCGCTGATGACCAG CTGGCATAGCATCAAATTTATCAACCCGAAAAA CGATGGTGCCATTCTGCCGATTCTGGATCTGA ATGGCTTTAAAATCAGCAATCCGACCCTGTTTG CACGTACCAGTGATGTTGATATCCGCAAATTTT TCGAAGGTCTGGGTTATAGTCCGCGTTATATT GAAAACGATGACATCCATGACTACATGGCCTA TCATAAACTGGCAGCAGAAGTTTTTGACAAAG CCATTGAAGATATCCATCAGATTCAGAAAGATG CCCGTGAAGATAATCGCTATCAGAATGGTGAA ATTCCGGCATGGCCGATTGTTATTGCACGTCT GCCGAAAGGTTGGGGTGGTCCTCGTTATAATG ATTGGAGCGGTCCGAAATTTGATGGTAAAGGT ATGCCGATCGAACATAGCTTTCGTGCACATCA GGTTCCGCTGCCGCTGAGCAGCAAAAACATG GGCACCCTGCCGGAATTTGTTAAATGGATGAC CAGCTATCAGCCGGAAACCCTGTTTAATGCAG ATGGTAGCCTGAAAGAAGAACTGCGCGATTTT GCACCGAAAGGTGAAATGCGTATGGCAAGCAA TCCGGTTACCAATGGTGGTGTTGATTATAGCA ATCTGGTTCTGCCGGATTGGCAAGAATTTGCA AATCCGATTAGCGAAAACAATCGTGGTAAACT GCTGCCGGATACCAATGATAATATGGATATGA ACGTGCTGAGCAAATATTTCGCCGAAATTGTTA AACTGAACCCGACCCGTTTTCGTCTGTTTGGT CCGGATGAAACCATGAGCAATCGTTTTTGGGA GATGTTTAAAGTGACCAATCGTCAGTGGATGC AGGTTATCAAAAATCCGAACGATGAGTTTATTA GTCCGGAAGGTCGCATTATTGATAGCCAGCTG AGCGAACATCAGGCAGAAGGTTGGCTGGAAG GTTATACCCTGACCGGTCGTACCGGTGTTTTT GCAAGCTATGAAAGTTTTCTGCGTGTTGTTGAT AGCATGCTGACCCAGCACTTTAAATGGATTCG TCAGGCAGCAGATCAGAAATGGCGTCATGATT ATCCGAGCCTGAATGTTATTAGCACCAGCACC GTTTTTCAGCAGGATCATAATGGTTATACCCAT CAAGATCCGGGTATGCTGACCCATCTGGCAGA GAAAAAAGCGATTTTATTCGTCAGTATCTGCC TGCAGATGGTAATACCCTGCTGGCCGTTTTTG ATCGTGCATTTCAGGATCGCAGCAAAATTAAC CATATTGTTGCAAGCAAACAGCCTCGTCAGCA GTGGTTTACCAAAGAAGAAGCAGAAAAACTGG CCACCGATGGTATTGCAACCATTGATTGGGCA AGCACCGCAAAAGATGGTGAAGCCGTTGATCT GGTTTTTGCAAGTGCCGGTGCAGAACCGACCA TTGAAACCCTGGCAGCACTGCATCTGGTTAAT | The restriction sites for PacI and NotI are underlined. | SQ 0005 |

TABLE 3-continued

Sequences of bacterial chromosomal regions, genes used, plasmids regions.

| Name | Nucleotide sequence | Description | SEQ ID NO |
|---|---|---|---|
| | GAAGTTTTTCCGCAGGCCAAATTTCGCTATGTT<br>AATGTTGTTGAACTGGGTCGTCTGCAGAAAAA<br>GAAAGGTGCACTGAATCAAGAACGCGAACTGA<br>GTGATGAAGAGTTCGAAAAATACTTTGGTCCG<br>AGCGGTACACCGGTTATTTTTGGTTTTCATGGC<br>TATGAAGATCTGATCGAGAGCATCTTTTATCAG<br>CGTGGTCATGATGGTCTGATTGTTCATGGTTAT<br>CGTGAAGATGGTGATATTACCACCACCTATGA<br>TATGCGTGTTTATAGCGAACTGGATCGTTTTCA<br>TCAGGCAATTGATGCAATGCAGGTTCTGTATG<br>TGAATCGTAAAGTTAATCAGGGTCTGGCCAAA<br>GCATTTATTGATCGTATGGAACGTACCCTGGT<br>GAAACATTTTGAAGTTACCCGTAATGAAGGCG<br>TTGATATTCCGGAATTTACCGAATGGGTTTGGA<br>GCGATCTGAAAAAGTAATGAGCGGCCGC | | |
| MCS of the pGB0124 plasmid | GAATTCGAGCTCGGTACCCGGGGATCCTCTAG<br>AGGCATGCCTAGGTTTAAACTAAGGAGGTTAA<br>TTAACCCCGCGGCCGCAAGCTT | | SQ 0006 |

TABLE 4

Primer sequence

| Name | Sequence | Description | SEQ ID NO: |
|---|---|---|---|
| 0635 | Ggttcaattcttcctttagcggc | Primer for sequencing the E.coli chromosomal region including the ptsHI genes. | RC0001 |
| 0638 | Ccgcaaaaacgacatccggcacg | Primer for sequencing the E.coli chromosomal region including the ptsHI genes. | RC0002 |
| 0633 | caagtatacccggcttaagtaccgggttagttaa<br>cttaaggagaatgacAGAGCGGCCGCC<br>ACCGCGGG | Primer for deletion of the zwf_edd_eda genes. | RC0003 |
| 0634 | gcaaaaaaacgctacaaaaatgcccgatcctc<br>gatcgggcatttttgacttGCATATGCTGCG<br>TGCATGCG | Primer for deletion of the zwf_edd_eda genes. | RC0004 |
| 1036 | Ccgcactttgcgcgcttttccc | Primer for sequencing the E.coli chromosomal region including the zwf_edd_eda genes. | RC0005 |
| 1037 | Ggtgattttcagtgaggtctcccc | Primer for sequencing the E.coli chromosomal region including the zwf_edd_eda genes. | RC0006 |
| 0629 | agacttccggcaacagatttcattttgcattccaa<br>agttcagaggtagtcAGAGCGGCCGCC<br>ACCGCGGG | Primer for deletion of the pfkA gene. | RC0007 |
| 0630 | gcttctgtcatcggtttcagggtaaaggaatctgc<br>cttttttccgaaatcaGCATATGCTGCGTG<br>CATGCG | Primer for deletion of the pfkA gene. | RC0008 |
| 0619 | Ggcgctcacgatcttcgcacgcggc | Primer for sequencing the E.coli chromosomal region including the pfkA gene. | RC0009 |
| 0620 | Ccgcctcatattgctgacaaagtgcgc | Primer for sequencing the E.coli chromosomal region including the pfkA gene. | RC0010 |
| 0631 | actttccgctgattcggtgccagactgaaatcagc<br>ctataggaggaaatgAGAGCGGCCGCC<br>ACCGCGGG | Primer for deletion of the pfkB gene. | RC0011 |

TABLE 4-continued

Primer sequence

| Name | Sequence | Description | SEQ ID NO: |
|---|---|---|---|
| 0632 | gttgccgacaggttggtgatgattcccccaatgct gggggaatgtttttgGCATATGCTGCGT GCATGCG | Primer for deletion of the pfkB gene. | RC0012 |
| 0621 | Ccacagcgaccaggcagtggtgtgtcc | Primer for sequencing the E.coli chromosomal region including the pfkB gene. | RC0013 |
| 0622 | Gcactttgggtaagccccgaaacc | Primer for sequencing the E.coli chromosomal region including the pfkB gene. | RC0014 |
| pUC1 8_24 6 | Ccattcaggctgcgcaactg | Primer for sequencing the phosphoketolase gene from Lactococcus lactis cloned into the pGB0123. | RC0015 |
| pUC1 8_38 00_re v | Gcgcgttggccgattcattaatgc | Primer for sequencing the phosphoketolase gene from Lactococcus lactis cloned into the pGB0123. | RC0016 |
| Pkt lacto 700_ dir | CAATCCGACCCTGTTTGCACGTA C | Primer for sequencing the phosphoketolase gene from Lactococcus lactis cloned into the pGB0123. | RC0017 |
| Pkt_l acto_ mil_di r | GCTGCCGGATACCAATGATAATA TGG | Primer for sequencing the phosphoketolase gene from Lactococcus lactis cloned into the pGB0123. | RC0018 |
| Pkt_l acto_ mil_re v | CCATATTATCATTGGTATCCGGCA GC | Primer for sequencing the phosphoketolase gene from Lactococcus lactis cloned into the pGB0123. | RC0019 |
| 0070 | CCCGGGGGATCCAGAATTTAAAA GGAGGGATT | Primer for amplifying the ctfA and cffB genes from Clostridium acetobutylicum ATCC 824 strain. | RC0020 |
| 0071 | CTCGAGGATATCAAGAATTCTTTT TAAACAGCCATGGGTC | Primer for amplifying the ctfA and cffB genes from Clostridium acetobutylicum ATCC 824 strain. | RC0021 |
| 1066 | TGTAAAACGACGGCCAGT | General primer for sequencing | RC0022 |
| 1067 | CAGGAAACAGCTATGACC | General primer for sequencing | RC0023 |
| 0072 | CTCGAGGATATCAGGAAGGTGAC TTTTATGTTAAAGG | Primer for amplifying the adc gene from the Clostridium acetobutylicum ATCC 824 strain. | RC0024 |
| 0073 | GCATGCGTCGACATTAAAAAAATA AGAGTTACC | Primer for amplifying the adc gene from Clostridium acetobutylicum ATCC 824 strain | RC0025 |
| 1068 | CCTCACGGCAAAGTCTCAAGC | Primer for sequencing the ctfA and cffB genes | RC0026 |
| 1069 | GCCATGGGTCTAAGTTCATTGG | Primer for sequencing the ctfA and cffB genes | RC0027 |
| 0074 | CATGATTTTAAGGGGGGTACCAT ATGCATAAGTTTAA ATCC 824 strain | Primer for amplifying the thl gene from Clostridium acetobutylicum | RC0028 |
| 0075 | GTTATTTTTAAGGATCCTTTTTAG CACTTTTCTAGC | Primer for amplifying the thl gene from Clostridium acetobutylicum ATCC 824 strain | RC0029 |

TABLE 4-continued

Primer sequence

| Name | Sequence | Description | SEQ ID NO: |
|---|---|---|---|
| 1070 | GGCAGAAAGGGAGAAACTGTAG | Primer for sequencing the acetone operon from *Clostridium acetobutylicum* (ATCC 824) | RC0030 |
| 1071 | TGGAAAGAATACGTGCAGGCGG | Primer for sequencing the acetone operon from *Clostridium acetobutylicum* (ATCC 824) | RC0031 |
| 1072 | GATTACGCCAAGCTTGCATGCC | Primer for sequencing the acetone operon from *Clostridium acetobutylicum* (ATCC 824) | RC0032 |
| 1073 | CCGGCCTCATCTACAATACTACC | Primer for sequencing the acetone operon from *Clostridium acetobutylicum* (ATCC 824) | RC0033 |
| 1074 | CCCATTATTGCTGGGTCAACTCC | Primer for sequencing the acetone operon from *Clostridium acetobutylicum* (ATCC 824) | RC0034 |
| 1516 | CCCGGTACCTCATTACTTTTTCAGATCGCTCCAAACCC | Primer for amplifying the phosphoketolase gene (YP_003354041.1) from *Lactococcus lactis*. | RC0035 |
| 1517 | GGGGAATTCAGGAGGTGTACTAGATGCATCATCACCACCATCACATGACC | Primer for amplifying the phosphoketolase gene (YP_003354041.1) from *Lactococcus lactis*. | RC0036 |
| 1994 | CCATAGCTCCACCCATACCAGAGAGC | Primer for sequencing the acetone operon from *Clostridium acetobutylicum* (ATCC 824) | RC0037 |
| 1995 | GCTATTATTACGTCAGCATCTCCTGC | Primer for sequencing the acetone operon from *Clostridium acetobutylicum* (ATCC 824) | RC0038 |
| 1996 | GCAGGCGAAGTTAATGGCGTGC | Primer for sequencing the acetone operon from *Clostridium acetobutylicum* (ATCC 824) | RC0039 |
| 1997 | GATACGGGGTAACAGATAAACCATTTC | Primer for sequencing the acetone operon from *Clostridium acetobutylicum* (ATCC 824) | RC0040 |
| 1998 | CCCTTTCTGCCTTTAATTACTACAGG | Primer for sequencing the acetone operon from *Clostridium acetobutylicum* (ATCC 824) | RC0041 |
| 1999 | GCATCAGGATTAAATGACTGTGCAGC | Primer for sequencing the acetone operon from *Clostridium acetobutylicum* (ATCC 824) | RC0042 |
| 2000 | GGACTAGCGCCCATTCCAACTATTCC | Primer for sequencing the acetone operon from *Clostridium acetobutylicum* (ATCC 824) | RC0043 |
| 2001 | GCTGCAAGGCGATTAAGTTGGGTAACGCC | Primer for sequencing the acetone operon from *Clostridium acetobutylicum* (ATCC 824) | RC0044 |
| 2002 | GCATTGCGTGTACAAGAGTAACGAG | Primer for sequencing the acetone operon from *Clostridium acetobutylicum* (ATCC 824) | RC0045 |
| 2003 | CCTGTCCAAGCTTCATGTACGG | Primer for sequencing the acetone operon from *Clostridium acetobutylicum* (ATCC 824) | RC0046 |
| 1109 | GCGCAAGATCATGTTACCGGTAAAATAACCATAAAGGATAAGCGCAGATAGCATATGCTGCGTGCATGCG | Primer for deletion of the zwf gene. | RC0047 |

TABLE 4-continued

Primer sequence

| Name | Sequence | Description | SEQ ID NO: |
|---|---|---|---|
| 1110 | CGCCTGTAACCGGAGCTCATAGGG | Primer for sequencing the E.coli chromosomal region including the zwf gene. | RC0048 |

Chromosomal Integration for Gene Knockouts.

To integrate DNA into a specific region of the chromosome, homology of the inserting DNA to the targeted chromosomal site and a selectable marker are required. It is advantageous if the marker can be easily removed after integration. The FRT/Flp recombinase system provides a mechanism to remove the marker. The FRT sites are recognition sites for the Flp recombinases. Flp is a site specific recombinase, which excises the intervening DNA from the directly repeated recognition sites.

The integration cassette containing homologous arms to the targeted chromosomal site and encoding a selectable marker flanked by FRT (Datsenko K A. And Wanner B L., Proceedings of the National Academy of Sciences, 2000, Vol. 97, No. 12, pp. 6640-6645) sites is transformed into target cells harboring pKD46 (Datsenko K A. And Wanner B L., Proceedings of the National Academy of Sciences, 2000, Vol. 97, No. 12, pp. 6640-6645). Successful integrants are selected by growth of the cells in the presence of the antibiotic. Subsequently, pKD46 is cured from the cells and the recombinase plasmid is then introduced into the integrants for removal of the antiobiotic gene. Strains containing a FRT cassette are transformed with the pCP20 plasmid that encodes Flp recombinase (Datsenko K A. And Wanner B L., Proceedings of the National Academy of Sciences, 2000, Vol. 97, No. 12, pp. 6640-6645). After removal of the integrated marker, the recombinase plasmids are cured from the strain.

Example 1: Construction of Strain GBE1014

The purpose of this section is to describe the construction of an *Escherichia coli* strain, named GBE1014, for which the PEP-dependent glucose uptake is inactivated by deletion of the PTS transport genes, the ATP-dependent glucose uptake is enabled, the Embden-Meyerhof-Parnas pathway (EMPP) is inactivated by deletion of the phosphofructokinase genes, and the pentose phosphate pathway (PPP) is inactivated by deletion of the glucose-6-phosphate dehydrogenase gene.

Construction started with strain GBE0901. GBE0901 is an *Escherichia coli*, (Migula) Castellani and Chalmers, strain MG1655 (ATCC #700926) where the original nucleotidic sequence, from bp 2531736 to 2533865 (NCBI genome database), included the ptsH and ptsI genes, was replaced by SEQ S00001. This deletion affects the PEP-dependent phosphotransferase system (PTS), resulting in the PEP-dependent glucose uptake to be inactivated in strain GBE0901. Deletion of the ptsHI genes was verified by PCR and oligonucleotides 0635 and 0638 (given as SEQ RC0001 and RC0002, respectively) were used as primers. The resulting 0.4 Kbp PCR product was sequenced using the same primers.

Strain GBE0901 was cultivated in LB medium and GBE0901 cells were made electrocompetent. Electrocompetent GBE0901 cells were transformed with a plasmid named pKD46 (Datsenko K A. And Wanner B L., Proceedings of the National Academy of Sciences, 2000, Vol. 97, No. 12, pp. 6640-6645) and then plated on LB plates containing ampicilline (100 ug/ml). Plates were incubated overnight at 30° C. Transformation of GBE0901 cells with plasmid pKD46 generated strain GBE0902. The plasmid pGBE0688 presents a resistance gene to spectinomycin placed under the control of its own promoter. The sequence of this resistance cassette is indicated in table 3 (SEQ SQ0002).

Plasmid pGBE0688 was used as a template with primers 0633 and 0634 (given as SEQ RC0003 and RC0004, respectively) to generate a 1.3 Kbp PCR product. This 1.3 Kbp PCR product was transformed into electrocompetent GBE0902 bacteria and the transformation mixture was then plated on LB plates containing spectinomycin (50 ug/ml) and incubated overnight at 37° C. to generate strain GBE0903. In strain GBE0903 the DNA sequence composed by the zwf, edd, and eda genes were deleted. These genes respectively code for a glucose-6-phosphate dehydrogenase, a 6-phosphogluconate dehydratase, and a 2-keto-3-deoxy-6-phosphogluconate aldolase. This deleted DNA sequence including the zwf, edd, and eda genes was replaced by a spectinomycin resistance cassette. In order to check the effective deletion of the zwf, edd, and eda genes, a PCR amplification was performed with primers 1036 and 1037 (given as SEQ RC0005 and RC0006, respectively). A final 1.9 Kbp PCR product was obtained. This 1.9 Kbp PCR product was sequenced with the same primers 1036 and 1037.

Strain GBE0903 was then plated on LB plates, incubated at 37° C. and isolated colonies were screened on MS plates (Richaud C., Mengin-Leucreulx D., Pochet S., Johnson E J., Cohen G N. and Marhere P; The Journal of Biological Chemistry; 1993; Vol. 268; No. 36; pp. 26827-26835) with glucose as the source of carbon (2 g/L). After 48 hours of incubation at 37° C., colonies became visible and were transferred to an MS liquid medium supplied with glucose (2 g/L). This overnight incubation at 37° C. induced the loss of the pKD46 plasmid. One isolate had a doubling time of 7 hours and was named GBE1000.

Strain GBE1000 was made electrocompetent. GBE1000 electrocompetent cells were transformed with plasmid pKD46, and then plated on LB plates supplied with ampicilline (100 ug/ml). Plates were incubated overnight at 30° C. Transformation of GBE1000 cells with plasmid pKD46 generated strain GBE1001.

The plasmid pGBE0687 presents a resistance gene to apramycin placed under the control of its own promoter. The sequence of this resistance cassette is indicated in table 3 (SEQ SQ0003).

The plasmid pGBE0687 was used as a template along with primers 0629 and 0630 (given as SEQ RC0007 and RC0008, respectively) to generate a 1.2 Kbp PCR product. The resulting 1.2 Kbp PCR product was transformed into electrocompetent GBE1001 bacteria and the transformation mixture was plated on LB plates containing apramycin (50 ug/ml). Plates were then incubated overnight at 37° C. to generate a new strain named GBE1005_pKD46. In Strain GB1005_pKD46 the phosphofructokinase gene pfkA, was deleted and was replaced by the apramycin resistance cassette. To check that the deletion of the pfkA gene occurred, a PCR amplification was performed with primers 0619 and 0620 (given as SEQ RC0009 and RC0010, respectively). This 1.7 Kbp PCR product was sequenced with the same primers 0619 and 0620. In order to check the loss of the plasmid pKD46, the strain GBE1005_pKD46 was plated on LB plates and incubated overnight at 42° C. The loss of the plasmid pKD46 was verified by plating isolated colonies on LB plates containing ampicilline (100 ug/ml), incubated overnight at 30° C., and on LB plates incubated overnight at 37° C. The resulting strain grew on LB plates incubated at 37° C. and was named GBE1005. GBE1005 cells did not grow on LB plates supplied with ampicilline (100 ug/ml).

The spectinomycin cassette was located at the corresponding loci of the zwf_edd_eda genes and the apramycin cassette was located at the corresponding loci of the pfkA genes. In order to excise the resistant cassettes containing the spectinomycin and apramycin resistance genes, the strain GBE1005 was transformed with the plasmid pCP20 (Datsenko K A. And Wanner B L., Proceedings of the National Academy of Sciences, 2000, Vol. 97, No. 12, pp. 6640-6645) to obtain the strain GBE1005_p. After overnight incubation on LB plates containing ampicilline (100 ug/ml) at 30° C., isolated colonies were restreaked on LB plates supplied with ampicilline (100 ug/ml) and incubated overnight at 30° C. Isolated colonies were then plated on LB plates and incubated overnight at 42° C. which caused the loss of the pCP20 plasmid. Then, in order to check the effective excision of the two resistant cassettes and the loss of the pCP20 plasmid, isolated colonies were streaked out on LB plates containing spectinomycin (50 ug/ml), incubated overnight at 37° C., on LB plates containing apramycin (50 ug/ml), incubated overnight at 37° C., on LB plates containing ampicilline (100 ug/ml), incubated overnight at 30° C. and on LB plates, incubated overnight at 37° C. The resulting strain grew on LB plates incubated at 37° C. and was named GBE1006. GBE1006 cells did not grow on LB plates containing spectinomycin (50 ug/ml), on LB plates containing apramycin (50 ug/ml), and on LB plates supplied with ampicilline (100 ug/ml).

Strain GBE1006 was made electrocompetent, and GBE1006 electrocompetent cells were transformed with plasmid pKD46. Transformant cells were then plated on LB plates containing ampicilline (100 ug/ml) and plates were incubated overnight at 30° C. to obtain a new strain named GBE1010. A PCR product was generated by using the plasmid pGBE0688 as a template and the oligonucleotides 0631 and 0632 (given as SEQ RC0011 and RC0012, respectively) as primers. The resulting 1.3 Kbp PCR product was transformed into electrocompetent GBE1010 bacteria and the transformation mixture was plated on LB plates containing spectinomycin (50 ug/ml). Plates were incubated overnight at 37° C. to generate strain GBE1014_pKD46. In Strain GBE1014_pKD46 the phosphofructokinase gene pfkB, was deleted and the deleted DNA sequence was replaced by a cassette containing the spectinomycin resistance gene. To check that the deletion of the pfkB gene occurred, a PCR amplification was performed with primers 0621 and 0622 (given as SEQ RC0013 and RC0014, respectively). This final 2.2 Kbp PCR product was sequenced by using the same primers 0621 and 0622.

In order to induce the loss of the plasmid pKD46, strain GBE1014_pKD46 was plated on LB plates and plates were incubated overnight at 42° C. The loss of the plasmid pKD46 was checked by plating isolated colonies on LB plates supplied with ampicilline (100 ug/ml), incubated overnight at 30° C., and on LB plates incubated overnight at 37° C. The resulting strain growing on LB plates incubated at 37° C. was named GBE1014. GBE1014 cells did not grow on LB plates supplied with ampicilline (100 ug/ml).

Example 2 Construction of Strain GBE0929

Strain. GBE0901 was plated on LB plates at 37° C. and isolated colonies were screened on MS plates with glucose as the source of carbon (2 g/L). After 48 hours of incubation at 37° C., colonies became visible. One isolate had a doubling time of 5 hours and was named GBE0929.

Example 3: Construction of Strain GBE1344

Construction started with the strain named GBE0129. GBE0129 is an MG1655 *Escherichia coli* bacteria (ATCC #700926).

Strain GBE0129 was cultivated in LB medium and GBE0129 cells were made electrocompetent. Electrocompetent GBE0129 cells were transformed with plasmid pKD46, and then transformants were plated on LB plates containing ampicilline (100 ug/ml). Plates were incubated overnight at 30° C. to generate a new strain named GBE0170.

A PCR product was generated using plasmid pGBE0687 as a template and oligonucleotides 0633 and 0634 (given as SEQ RC0003 and RC0004, respectively) as primers. The resulting 1.2 Kbp PCR product was transformed into electrocompetent GBE0170 bacteria and the transformation mixture was plated on LB plates containing apramycin (50 ug/ml). Plates were incubated overnight at 37° C. This incubation triggered the loss of the pKD46 plasmid and led to the creation of a new strain named GBE1339. In Strain GBE1339 the glucose-6-phosphate dehydrogenase encoded by the zwf gene, the 6-phosphogluconate dehydratase encoded by the edd gene and the 2-keto-3-deoxy-6-phosphogluconate aldolase encoded by the eda gene were inactive. The sequential zwf, edd, and eda genes were deleted and replaced by a cassette containing the apramycin resistance gene. To check that the deletion of the zwf, edd, and eda genes was effective, a PCR amplification was performed with primers 1036 and 1037 (given as SEQ RC0005 and RC0006, respectively). This 1.8 Kbp PCR product was sequenced with the same primers 1036 and 1037.

Strain GBE1339 was made electrocompetent, and GBE1339 electrocompetent cells were transformed with plasmid pKD46. Transformants were then plated on LB plates supplied with ampicilline (100 ug/ml). Plates were incubated overnight at 30° C. to generate strain GBE1340. A PCR product was performed by using plasmid pGBE0688 as a template and oligonucleotides 0629 and 0630 (given as SEQ RC0007 and RC0008, respectively) as primers. The resulting 1.3 Kbp PCR product was transformed into electrocompetent GBE1340 bacteria and the transformation mixture was plated on LB plates containing spectinomycin (50 ug/ml). Plates were incubated overnight at 37° C. to generate strain GBE1341_pKD46. In Strain GB1341_pKD46 the pfka gene coding for a phosphofructokinase was replaced by the spectinomycin resistance gene. To check that the deletion of the pfkA gene was effective, a PCR amplification was performed with primers 0619 and 0620 (given as SEQ RC0009 and RC0010, respectively). This 1.8 Kbp PCR product was sequenced with the same primers 0619 and 0620. In order to induce the loss of the plasmid pKD46 for the strain GBE1341_pKD46, GBE1341_pKD46 cells were plated on LB plates and incubated at 42° C. The loss of the plasmid pKD46 was verified by plating isolated colonies on LB plates supplied with ampicilline (100 ug/ml), incubated overnight at 30° C. and on LB plates incubated overnight at 37° C. The resulting strain growing on LB plates incubated at 37° C. was GBE1341. GBE1341 did not grow on LB plates supplied with ampicilline (100 ug/ml).

In order to excise the resistant cassettes containing the apramycin and spectinomycin resistance genes, which were respectively located in the former loci of the zwf_edd_eda and pfkA genes, the strain GBE1341 was transformed with plasmid pCP20 to obtain a new strain named GBE1341_p. After overnight incubation on LB plates containing ampicilline (100 ug/ml) at 30° C., isolated colonies were restreaked on LB plates supplied with ampicilline (100 ug/ml) for another overnight incubation at 30° C. Isolated colonies were then plated on LB plates and incubated overnight at 42° C. This incubation at 42° C. triggered the loss of the pCP20 plasmid. Eventually in order to check excision of the two resistant cassettes and the loss of the pCP20 plasmid, isolated colonies were streaked out on LB plates containing spectinomycin (50 ug/ml) and incubated overnight at 37° C., on LB plates supplied with apramycin (50 ug/ml) and incubated overnight at 37° C., on LB plates containing ampicilline (100 ug/ml) and incubated overnight at 30° C. and on LB plates incubated overnight at 37° C. The generated strain growing on LB plates incubated at 37° C. was named GBE1342. GBE1342 cells did not grow on LB plates supplied with spectinomycin (50 ug/ml), on LB plates supplied with apramycin (50 ug/ml) and on LB plates containing ampicilline (100 ug/ml).

Strain GBE1342 was made electrocompetent, and GBE1342 cells were transformed with plasmid pKD46. Transformants were then plated on LB plates supplied with ampicilline (100 ug/ml) and incubated overnight at 30° C. to obtain strain GBE1343. A PCR product was performed and used the plasmid pGBE0688 as a template and oligonucleotides 0631 and 0632 (given as SEQ RC0011 and RC0012, respectively) as primers. The resulting 1.3 Kbp PCR product was transformed into electrocompetent GBE1343 bacteria and the transformation mixture was plated on LB plates containing spectinomycin (50 ug/ml) followed by an overnight incubation at 37° C. A new strain was generated and named GBE1344_pKD46. In Strain GBE1344_pKD46 the pfkb gene coding for a phosphofructokinase was deleted and replaced by the spectinomycin resistance cassette. To check that the deletion of the pfkB gene was effective, a PCR amplification was performed with primers 0621 and 0622 (given as SEQ RC0013 and RC0014, respectively). The 2.2 Kbp PCR product obtained was sequenced with the same primers 0621 and 0622.

In order to induce the loss of the plasmid pKD46, the strain GBE1344_pKD46 was plated on LB plates and incubated overnight at 42° C. The loss of the plasmid pKD46 was checked by plating isolated colonies on LB plates containing ampicilline (100 ug/ml) and incubated overnight at 30° C. and on LB plates incubated overnight at 37° C. The generated strain growing on LB plates incubated at 37° C. was named GBE1344. GBE1344 cells did not grow on LB plates, containing ampicilline (100 ug/ml).

Example 4: Construction of Plasmid PGBE0457

The purpose of this section is to describe the construction of a plasmid that allows the expression of phosphoketolase YP_003354041.1 from *Lactococcus lactis* in *E. coli* strains.

The plasmid pGBE0123 is a modified version of the plasmid pUC18 (New England Biolabs) and contains a modified Multiple Cloning Site (MCS). The original MCS from pUC18 (from HindIII restriction site to EcoRI restriction site) was replaced by the sequence SQ0004 (table 3). The plasmid pGB0123 allows expression of two recombinant proteins under the control of the Plac promoter.

| Phospho-ketolase gene ID | Phospho-ketolase protein ID | Organism of origin | Plasmid from GeneArt ® (Invitrogen) |
|---|---|---|---|
| 8679043 | YP_003354041.1 | *Lactococcus lactis* subsp. *lactis* KF147 | pGBE0421 |

The *L. lactis* phosphoketolase gene was codon-optimized by GeneArt® (Invitrogen) for optimal expression in *Escherichia coli*. In addition, a His-tag was added at the 5' position of the gene and an additional stop codon was added at the 3' position (SQ0005). The gene construction is flanked by PacI and NotI restriction sites and provided within plasmid pGBE0421.

For cloning experiment, PCR products and restriction fragments were gel purified using QIAquick gel Extraction kit (Qiagen). Restriction enzymes and T4 DNA ligase (New England Biolabs, Beverly, Mass.) were used according to manufacturer's recommendations.

Plasmid pGBE0421 was digested with the restriction enzymes PacI and NotI to create a 2.6 Kbp product. The pGB0123 plasmid was digested as well with restriction enzymes, PacI and NotI and ligated to the 2.6 Kbp restriction fragment. The resulting plasmid (pGBE0457) was sequenced with primers 1061, 1062, 1063, 1064 and 1065 (given as SEQ RC0015, RC0016, RC0017, RC0018 and RC0019 respectively).

The expression of the phosphoketolase from *Lactococcus lactis* was checked on a protein gel, after purification of the recombinant protein using a His trap (Protino Ni-IDA 1000 kit, Macherey Nagel). Purification was processed according to the manufacturer's recommendations. Enzymatic assay, with purified enzyme, was also performed in order to detect phosphoketolase activity on two different substrates: xylulose-5-phosphate and fructose-6-phosphate. The experimental procedure was the same than the one used by Leo Meile et al., (Journal of Bacteriology, May 2001, p. 2929-2936), except that the pH of the solution was 7.5 and 1 mM of MgCl2 was added. For this enzymatic assay, 10 μg of purified protein was added to the 75 μl of the reaction. The specific activity (μmol of Acetyl-P formed/min/mg protein) was 2815 μmol/min/mg protein and 1941 μmol/min/mg protein for D-xylulose-5-phosphate and D-fructose-6-phosphate, respectively.

Example 5: Construction of Plasmid PGBE0096

The construction of the plasmids responsible for acetone production in *E. coli* was based on the plasmid construction described in Bermejo L L., Welker N E. and Papoutsakis E T., Applied and Environmental Microbiology, 1998, Vol. 64, No. 3, pp. 1076-1085.

The strain *Clostridium acetobutylicum* was ordered (ATCC 824). The genomic DNA from this strain is made up of a bacterial chromosome and a plasmid named pSOL1. The ctfA and ctfB genes were PCR amplified from the pSOL1 plasmid with primers 0070 and 0071 (given as SEQ RC0020 and RC0021, respectively). A BamHI restriction site at the 5' end of the PCR product and an EcoRV restriction site at the 3' end of the PCR product were introduced. The resulting 1.3 Kbp PCR product was digested with the restriction enzymes BamHI and EcoRV, then ligated with the pGB0689 (pBluescript II phagemids, Agilent Technologies) which was digested as well with restriction enzymes, BamHI and EcoRV. The resulting plasmid (pGBE0690) was sequenced with primers 1066 and 1067 (given as SEQ RC0022 and RC0023, respectively).

The adc gene and the gene terminator were PCR amplified from the pSOL1 plasmid with primers 0072 and 0073 (given as SEQ RC0024 and RC0025, respectively). PCR amplification allowed inserting an EcoRV restriction site at the 5' end and a SalI restriction site at the 3' end. The resulting 0.8 Kbp PCR product was digested with the restriction enzymes EcoRV and SalI. The pGBE0690 plasmid was digested as well with restriction enzymes, EcoRV and SalI and then ligated with the 0.8 Kbp PCR product. The resulting plasmid (pGBE0691) was sequenced with primers 1066, 1067, 1068 and 1069 (given as SEQ RC0022, RC0023, RC0026 and RC0027, respectively).

Plasmid pGBE0691 was digested with the restriction enzymes BamHI and SalI to create a 2.2 Kbp product. The 2.2 Kbp restriction fragment contained the ctfA, ctfB and adc genes. The pGBE0051 plasmid (pUC19, New England Biolabs) was digested as well with restriction enzymes, BamHI and SalI, and was then ligated with the 2.2 Kbp restriction fragment. The resulting plasmid (pGBE0692) was sequenced with primers 1066, 1067, 1068 and 1069 (given as SEQ RC0022, RC0023, RC0026 and RC0027, respectively).

The thl gene and its corresponding thl promoter from *Clostridium acetobutylicum* (ATCC 824) genomic DNA were PCR amplified with primers 0074 and 0075 (given as SEQ RC0028 and RC0029, respectively). PCR amplification allowed inserting a KpnI restriction site at the 5' end and a BamHI restriction site at the 3' end. The resulting 1.4 Kbp PCR product was digested with the restriction enzymes KpnI and BamHI, and likewise for the plasmid pGBE0692. The digested pGBE0692 plasmid was ligated with the 1.4 Kbp PCR product. The resulting plasmid, pGBE0693, was sequenced with primers 1066, 1067, 1068, 1069, 1070, 1071, 1072, 1073 and 1074 (given as SEQ RC0022, RC0023, RC0026 RC0027, RC0030, RC0031, RC0032, RC0033 and RC0034, respectively).

The plasmid pGBE0124 is a modified version of the plasmid pSU18 (Borja Bartolomé, Yolanda Jubete, Eduardo Martinez and Fernando de la Cruz, Gene, 1991, Vol. 102, Issue 1, pp. 75-78) and it contains a modified Multiple Cloning Site (MCS). The original MCS from pSU18 (from EcoRI restriction site to HindIII restriction site) was replaced by the sequence SEQ SQ006 (table 3). The plasmid pGB0124 allows expression of two recombinant proteins under the control of the Plac promoter. Plasmid pGBE0693 was digested with the restriction enzymes KpnI and SalI to create a 3.5 Kbp product. The pGBE0124 plasmid was digested as well with restriction enzymes KpnI and SalI, and then ligated to the 3.5 Kbp restriction fragment. The resulting plasmid (pGBE0096) was sequenced with primers 1066, 1067, 1068, 1069, 1070, 1071, 1072, 1073 and 1074 (given as SEQ RC0022, RC0023, RC0026 RC0027, RC0030, RC0031, RC0032, RC0033 and RC0034, respectively).

Example 6: Acetone Production by the Strains GBE1346 and GBE1347

Description of Plasmid Transformation into Relevant Strains

The strain GBE0129 was made electrocompetent, and GBE0129 electrocompetent cells were transformed with plasmid pGBE0096. Transformants were then plated on LB plates containing chloramphenicol (25 ug/ml) and plates were incubated overnight at 30° C. to generate strain GBE0329.

Strain GBE1344 was made electrocompetent, and GBE1344 electrocompetent cells were transformed with both plasmids pGBE0457 and pGBE0096. Transformants were then plated on LB plates supplied with ampicilline (100 ug/ml) and chloramphenicol (25 ug/ml). Plates were incubated overnight at 30° C. to obtain strain GBE1345.

Isolated colonies from strains GBE0329 and GBE1345 were screened on MS plates containing glucose as the source of carbon (2 g/L) and chloramphenicol (25 ug/ml). These plates were incubated at 30° C. to obtain strains GBE1346 and GBE1347 respectively. After 4 days of incubation at 30° C., colonies were transferred to MS liquid, medium containing glucose (2 g/L) and chloramphenicol (25 ug/ml) and incubated 3 days at 30° C.

Description of Flasks Conditions

For the fermentation experiments, a MS medium with 200 mM of dipotassium phosphate was used instead of 50 mM dipotassium phosphate. The resulted medium was named MSP.

400 ml of MSP liquid medium containing glucose (10 g/L) and chloramphenicol (25 ug/ml), were inoculated either with pre culture of strain GBE1346 or with pre culture of strain GBE1347. The initial $OD_{600}$ was 0.1. The 400 ml of culture were incubated in 500 ml bottles, sealed with a screw cap, at 30° C., 170 rpm of speed. 2 ml aliquots were taken after 1 day, 2 days, 3 days, 6 days, 7 days and 8 days. For each aliquot samples, bottles were open during 10 seconds.

Description of Analytical Methods

Aliquots were filtered and the glucose concentration was determined with the glucose (HK) Assay kit (GAHK20-1KT, Sigma) according to manufacturer's recommendations. The acetone concentration was determined by gas chromatography using Gas chromatograph 450-GC (Bruker) and the following program:

Column: DB-WAX (123-7033, Agilent Technologies)

Injector Split/Splitless: T°=250° C.

Oven:

80° C. for 6 minutes

10° C. per minutes until 220° C.

220° C. for 7 minutes

Column flow: 1.5 ml/minute (Nitrogen)

Detector FID: T°=300° C.

Results

The ratio [acetone]produced (mM)/[glucose]consumed (mM) is higher for the strain GBE1347 than for the strain GBE1346.

Example 7: Acetone Production by the Strains GBE1350 and GBE1351

Description of Plasmid Transformation into Relevant Strains

Strain GBE0929 was made electrocompetent, and GBE0929 electrocompetent cells were transformed with a plasmid named pGBE0096. Transformants were then plated on LB plates supplied with chloramphenicol (25 ug/ml) and plates were incubated overnight at 30° C. to obtain strain GBE1348.

Strain GBE1014 were made electrocompetent, transformed with both plasmids pGBE0457 and pGBE0096. Transformants were then plated on LB plates supplied with ampicilline (100 ug/ml) and chloramphenicol (25 ug/ml) and plates were incubated overnight at 30° C. to obtain strain GBE1349.

Isolated colonies from strains GBE1348 and GBE1349 were screened on MS plates containing glucose as the source of carbon (2 g/L) and chloramphenicol (25 ug/ml). These plates were incubated 4 days at 30° C. to obtain strain GBE1350 and GBE1351 respectively. Isolated colonies were then transferred to MS liquid medium containing glucose (2 g/L) and chloramphenicol (25 ug/ml). GBE1350 and GBE1351 Cells were incubated at 30° C.

Description of Flasks Conditions 400 ml of MSP medium containing glucose (10 g/L) and chloramphenicol (25 ug/ml) were inoculated either with pre-culture of strain GBE1350 or with pre-culture of strain GBE1351. The initial $OD_{600}$ was 0.1. The 400 ml of culture were incubated in 500 ml bottles, sealed with a screw cap, at 30° C., 170 rpm of speed. 2 ml aliquots were taken after 1 day, 2 days, 3 days, 6 days, 7 days and 8 days. For each aliquot samples, bottles were opened during 10 seconds.

Description of Analytical Methods

Aliquots were filtered and the glucose concentration was determined with the glucose (HK) Assay kit (GAHK20-1KT, Sigma) according to manufacturer's recommendations. The acetone concentration was determined by gas chromatography using Gas chromatograph 450-GC (Bruker) and the following program:

Column: DB-WAX (123-7033, Agilent Technologies)
Injector Split/Splitless: T°=250° C.
Oven:
  80° C. for 6 minutes
  10° C. per minutes until 220° C.
  220° C. for 7 minutes
  Column flow: 1.5 ml/minute (Nitrogen)
Detector FID: T°=300° C.

Results

The ratio [acetone]produced (mM)/[glucose]consumed (mM) was higher for the strain GBE1351 than for the strain GBE1350.

Example 8: Construction of the Plasmid PGBE1020

The purpose of this section is to describe the construction of a plasmid that allows the expression of phosphoketolase YP_003354041.1 from *Lactococcus lactis* and also allows the production of acetone in *E. coli* strains.

The *L. Lactis* phosphoketolase gene was PCR amplified from the pGBE0421 plasmid with primers 1516 and 1517 (given as SEQ RC0035 and RC0036, respectively). PCR amplification allowed inserting an EcoRI restriction site and a Ribosome Binding Site (RBS) at the 5' end and a KpnI restriction site at the 3' end. The resulting 2.5 Kbp PCR product was digested with the restriction enzymes EcoRI and KpnI. The pGBE0123 plasmid was digested as well with restriction enzymes, EcoRI and KpnI and then ligated with the 2.5 Kbp PCR product. The resulting plasmid (pGBE0928) was sequenced with primers 1061, 1062, 1063, 1064 and 1065 (given as SEQ RC0015, RC0016, RC0017, RC0018 and RC0019, respectively).

Plasmid pGBE0096 was digested with the restriction enzymes KpnI and NotI to create a 3.6 Kbp product. The pGBE0928 plasmid was digested as well with restriction enzymes, KpnI and NotI and ligated to the 3.6 Kbp restriction fragment. The resulting plasmid (pGBE1020) was sequenced with primers 1994, 1995, 1996, 1997, 1998, 1999, 2000, 2001, 2002 and 2003 (given as SEQ RC0037, RC0038, RC0039, RC0040, RC0041, RC0042, RC0043, RC0044, RC0045 and RC0046, respectively).

Example 9: Construction of the Plasmid PGBE1021

The purpose of this section is to describe the construction of a plasmid that allows the production of acetone in *E. coli* strains.

Plasmid pGBE0096 was digested with the restriction enzymes KpnI and NotI to create a 3.6 Kbp product.

The pGBE0123 plasmid was digested as well with restriction enzymes, KpnI and Nott and then ligated with the 3.6 Kbp PCR product. The resulting plasmid (pGBE1021) was sequenced with primers 1994, 1995, 1996, 1997, 1998, 1999, 2000, 2001, 2002 and 2003 (given as SEQ RC0037, RC0038, RC0039, RC0040, RC0041, RC0042, RC0043, RC0044, RC0045 and RC0046, respectively).

Example 10: Acetone Production by the Strains GBE2264 and GBE2265

Description of Plasmid Transformation into Relevant Strains

The strain GBE0129 was made electrocompetent, and GBE0129 electrocompetent cells were transformed with plasmid pGB1021. Transformants were then plated on LB plates containing ampicilline (100 ug/ml) and plates were incubated overnight at 30° C. to generate strain GBE2262.

Strain GBE1344 was made electrocompetent, and GBE1344 electrocompetent cells were transformed with the plasmid pGBE1020. Transformants were then plated on LB plates supplied with ampicilline (100 ug/ml). Plates were incubated overnight at 30° C. to obtain strain GBE2263.

Isolated colonies from strains GBE2262 and GBE2263 were screened on MS plates containing glucose as the source of carbon (2 g/L) and ampicilline (100 ug/ml). These plates were incubated at 30° C. to obtain strains GBE2264 and GBE2265, respectively. After 4 days of incubation at 30° C., colonies were transferred to MS liquid medium containing glucose (2 g/L), yeast extract (0.1 g/L) and ampicilline (100 ug/ml) and incubated 3 days at 30° C.

Description of Flasks Conditions

MSP liquid medium (200 ml) containing glucose (10 g/L), yeast extract (0.1 g/L) and ampicilline (100 ug/ml), were inoculated either with pre culture of strain GBE2264 or with pre culture of strain GBE2265. The initial $OD_{600}$ was 0.1. The 200 ml of culture was incubated in 250 ml bottles, sealed with a screw cap, at 30° C., 170 rpm of speed. Aliquots (2 ml) were taken after 1 day, 2 days, 4 days, 5 days and 6 days. For each aliquot sample, the bottle was open for 10 seconds.

Description of Analytical Methods

Aliquots were filtered and the glucose concentration was determined by HPLC analysis using the Agilent HPLC (1260 Infinity) and a Hi-Plex Colomn (Agilent, PL1170-6830) with a guard column (Agilent, PL Hi-Plex H Guard Column, PL1170-1830).

Volume of injection: 20 μl
Solvent composition: $[H_{2SO4}]$: 5.5 mM
Temperature of the columns: 65° C.
RID (G1362A): temperature set: 35° C.

Acetone was extracted from the filtered aliquots by mixing with methyl acetate (1 volume of methyl acetate for 2 volumes of filtered aliquot). Acetone concentration was determined by gas chromatography using Gas chromatograph 450-GC (Bruker) and the following program:

Column: DB-WAX (123-7033, Agilent Technologies)
Injector:
  Split ratio: 10
  T°=250° C.
Oven:
  50° C. for 9 minutes
  20° C. per minute until 180° C.
  180° C. for 5 minutes
  Column flow: 1.5 ml/minute (Nitrogen)
Detector FID: T°=300° C.

Results

The ratio [acetone] produced (mM)/[glucose] consumed (mM) was higher for the strain GBE2265 than for the strain GBE2264.

Example 11: Construction of the Strain GBE1283

Strain GBE0929 was plated on MS plates containing glucose as the source of carbon (2 g/L). An isolated colony was transferred to MS liquid medium containing glucose (2 g/L) and incubated 3 days at 30° C. MS liquid medium (100 ml) containing glucose (2 g/L) was inoculated with pre culture of strain GBE0929. The initial $OD_{600}$ was 0.1. The 100 ml of culture was incubated in a 1 L erlenmeyer, at 30° C., 170 rpm of speed. When the $OD_{600}$ was superior to 1, an aliquot of the culture was taken and used as inoculum for a fresh culture (100 ml of culture incubated in 1 L erlenmeyer, at 30° C., 170 rpm of speed). Strain GBE0929 was subcultured 10 times to obtain strain GBE1283.

Example 12: Construction of the Strain GBE2256

Strain GBE1283 was cultivated in LB medium and GBE1283 cells were made electrocompetent. Electrocompetent GBE1283 cells were transformed with the pKD46 plasmid and then plated on LB plates containing ampicilline (100 ug/ml). Plates were incubated overnight at 30° C. Transformation of GBE1283 cells with plasmid pKD46 generated strain GBE1284.

The plasmid pGBE0688 was used as a template along with primers 0629 and 0630 (given as SEQ RC0007 and RC0008, respectively) to generate a 1.2 Kbp PCR product. The resulting 1.2 Kbp PCR product was transformed into electrocompetent GBE1284 bacteria and the transformation mixture was plated on LB plates containing spectinomycin (50 ug/ml). Plates were then incubated overnight at 37° C. to generate a new strain named GBE2252_pKD46. In Strain GB2252_pKD46 the phosphofructokinase gene pfkA, was deleted and was replaced by the spectinomycin resistance cassette. To check that the deletion of the pfkA gene occurred, a PCR amplification was performed with primers 0619 and 0620 (given as SEQ RC0009 and RC0010, respectively). This 1.7 Kbp PCR product was sequenced with the same primers 0619 and 0620. In order to check the loss of the plasmid pKD46, the strain GBE2252_pKD46 was plated on LB plates and incubated overnight at 42° C. The loss of the plasmid pKD46 was verified by plating isolated colonies on LB plates containing ampicilline (100 ug/ml), incubated overnight at 30° C., and on LB plates incubated overnight at 37° C. The resulting strain grew on LB plates incubated at 37° C. and was named GBE2252. GBE2252 cells did not grow on LB plates supplied with ampicilline (100 ug/ml).

Strain GBE2252 was made electrocompetent, and GBE2252 electrocompetent cells were transformed with plasmid pKD46. Transformant cells were then plated on LB plates containing ampicilline (100 ug/ml) and plates were incubated overnight at 30° C. to obtain a new strain named GBE2253.

A PCR product was generated by using the plasmid pGBE0687 as a template and the oligonucleotides 0631 and 0632 (given as SEQ RC0011 and RC0012, respectively) as primers. The resulting 1.3 Kbp PCR product was transformed into electrocompetent GBE2253 bacteria and the transformation mixture was plated on LB plates containing apramycin (50 ug/ml). Plates were incubated overnight at 37° C. to generate strain GBE2256_pKD46. In Strain GBE2256_pKD46 the phosphofructokinase gene pfkB, was deleted and the deleted DNA sequence was replaced by a cassette containing the apramycin resistance gene. To check that the deletion of the pfkB gene occurred, a PCR amplification was performed with primers 0621 and 0622 (given as SEQ RC0013 and RC0014, respectively). This final 2.2 Kbp PCR product was sequenced by using the same primers 0621 and 0622.

In order to induce the loss of the plasmid pKD46, strain GBE2256_pKD46 was plated on LB plates and plates were incubated overnight at 42° C. The loss of the plasmid pKD46 was checked by plating isolated colonies on LB plates supplied with ampicilline (100 ug/ml), incubated overnight at 30° C., and on LB plates incubated overnight at 37° C. The resulting strain growing on LB plates incubated at 37° C. was named GBE2256. GBE2256 cells did not grow on LB plates supplied with ampicilline (100 ug/ml).

Example 13: Construction of the Strain GBE1518

Plasmid pGBE0688 was used as a template with primers 0633 and 1109 (given as SEQ RC0003 and RC0047, respectively) to generate a 1.3 Kbp PCR product. This 1.3 Kbp PCR product was transformed into electrocompetent GBE1284 bacteria and the transformation mixture was then plated on LB plates containing spectinomycin (50 ug/ml) and incubated overnight at 37° C. to generate strain GBE1433. In strain GBE1433 the DNA sequence composed by the zwf gene were deleted. This deleted DNA sequence including the zwf gene was replaced by a spectinomycin resistance cassette. In order to check the effective deletion of the zwf gene, a PCR amplification was performed with primers 1036 and 1110 (given as SEQ RC0005 and RC0048, respectively). A final 1.5 Kbp PCR product was obtained. This 1.5 Kbp PCR product was sequenced with the same primers 1036 and 1110.

Strain GBE1433 was made electrocompetent. GBE1433 electrocompetent cells were transformed with plasmid pKD46, and then plated on LB plates supplied with ampicilline (100 ug/ml). Plates were incubated overnight at 30° C. Transformation of GBE1433 cells with plasmid pKD46 generated strain GBE1436.

The plasmid pGBE0687 was used as a template along with primers 0629 and 0630 (given as SEQ RC0007 and RC0008, respectively) to generate a 1.2 Kbp PCR product. The resulting 1.2 Kbp PCR product was transformed into electrocompetent GBE1436 bacteria and the transformation mixture was plated on LB plates containing apramycin (50 ug/ml). Plates were then incubated overnight at 37° C. to generate a new strain named GBE1441_pKD46. In Strain GB1441_pKD46 the phosphofructokinase gene pfkA, was deleted and was replaced by the apramycin resistance cassette. To check that the deletion of the pfkA gene occurred, a PCR amplification was performed with primers 0619 and 0620 (given as SEQ RC0009 and RC0010, respectively). This 1.7 Kbp PCR product was sequenced with the same primers 0619 and 0620. In order to check the loss of the plasmid pKD46, the strain GBE1441_pKD46 was plated on LB plates and incubated overnight at 42° C. The loss of the plasmid pKD46 was verified by plating isolated colonies on LB plates containing ampicilline (100 ug/ml), incubated overnight at 30° C., and on LB plates incubated overnight at 37° C. The resulting strain grew on LB plates incubated at 37° C. and was named GBE1441. GBE1441 cells did not grow on LB plates supplied with ampicilline (100 ug/ml).

The spectinomycin cassette was located at the corresponding loci of the zwf gene and the apramycin cassette was located at the corresponding loci of the pfkA gene. In order to excise the resistant cassettes containing the spectinomycin and apramycin resistance genes, the strain GBE1441 was transformed with the plasmid pCP20 to obtain the strain GBE1441_p. After overnight incubation on LB plates containing ampicilline (100 ug/ml) at 30° C., isolated colonies were restreaked on LB plates supplied with ampicilline (100 ug/ml) and incubated overnight at 30° C. Isolated colonies were then plated on LB plates and incubated overnight at 42° C. which caused the loss of the pCP20 plasmid. Then, in order to check the effective excision of the two resistant cassettes and the loss of the pCP20 plasmid, isolated colonies were streaked out on LB plates containing spectinomycin (50 ug/ml), incubated overnight at 37° C., on LB plates containing apramycin (50 ug/ml), incubated overnight at 37° C., on LB plates containing ampicilline (100 ug/ml), incubated overnight at 30° C. and on LB plates, incubated overnight at 37° C. The resulting strain grew on LB plates incubated at 37° C. and was named GBE1448. GBE1448 cells did not grow on LB plates containing spectinomycin (50 ug/ml), on LB plates containing apramycin (50 ug/ml), and on LB plates supplied with ampicilline (100 ug/ml).

Strain GBE1448 was made electrocompetent, and GBE1448 electrocompetent cells were transformed with plasmid pKD46. Transformant cells were then plated on LB plates containing ampicilline (100 ug/ml) and plates were incubated overnight at 30° C. to obtain a new strain named GBE1449. A PCR product was generated by using the plasmid pGBE0688 as a template and the oligonucleotides 0631 and 0632 (given as SEQ RC0011 and RC0012, respectively) as primers. The resulting 1.3 Kbp PCR product was transformed into electrocompetent GBE1449 bacteria and the transformation mixture was plated on LB plates containing spectinomycin (50 ug/ml). Plates were incubated overnight at 37° C. to generate strain GBE1518_pKD46. In Strain GBE1518_pKD46 the phosphofructokinase gene pfkB, was deleted and the deleted DNA sequence was replaced by a cassette containing the spectinomycin resistance gene. To check that the deletion of the pfkB gene occurred, a PCR amplification was performed with primers 0621 and 0622 (given as SEQ RC0013 and RC0014, respectively). This final 2.2 Kbp PCR product was sequenced by using the same primers 0621 and 0622.

In order to induce the loss of the plasmid pKD46, strain GBE1518_pKD46 was plated on LB plates and plates were incubated overnight at 42° C. The loss of the plasmid pKD46 was checked by plating isolated colonies on LB plates supplied with ampicilline (100 ug/ml), incubated overnight at 30° C., and on LB plates incubated overnight at 37° C. The resulting strain growing on LB plates incubated at 37° C. was named GBE1518. GBE1518 cells did not grow on LB plates supplied with ampicilline (100 ug/ml).

Example 14: Construction of the Strain GBE1420

Plasmid pGBE0688 was used as a template with primers 0633 and 0634 (given as SEQ RC0003 and RC0004, respectively) to generate a 1.3 Kbp PCR product. This 1.3 Kbp PCR product was transformed into electrocompetent GBE1284 bacteria and the transformation mixture was then plated on LB plates containing spectinomycin (50 ug/ml) and incubated overnight at 37° C. to generate strain GBE1287. In strain GBE1287 the DNA sequence composed by the zwf, edd, and eda genes were deleted. This deleted DNA sequence including the zwf, edd, and eda genes was replaced by a spectinomycin resistance cassette. In order to check the effective deletion of the zwf, edd, and eda genes, a PCR amplification was performed with primers 1036 and 1037 (given as SEQ RC0005 and RC0006, respectively). A final 1.9 Kbp PCR product was obtained. This 1.9 Kbp PCR product was sequenced with the same primers 1036 and 1037.

Strain GBE1287 was made electrocompetent. GBE1287 electrocompetent cells were transformed with plasmid pKD46, and then plated on LB plates supplied with ampicilline (100 ug/ml). Plates were incubated overnight at 30° C. Transformation of GBE1287 cells with plasmid pKD46 generated strain GBE1337.

The plasmid pGBE0687 was used as a template along with primers 0629 and 0630 (given as SEQ RC0007 and RC0008, respectively) to generate a 1.2 Kbp PCR product. The resulting 1.2 Kbp PCR product was transformed into electrocompetent GBE1337 bacteria and the transformation mixture was plated on LB plates containing apramycin (50 ug/ml). Plates were then incubated overnight at 37° C. to generate a new strain named GBE1353_pKD46. In Strain GB1353_pKD46 the phosphofructokinase gene pfkA, was deleted and was replaced by the apramycin resistance cassette. To check that the deletion of the pfkA gene occurred, a PCR amplification was performed with primers 0619 and 0620 (given as SEQ RC0009 and RC0010, respectively). This 1.7 Kbp PCR product was sequenced with the same primers 0619 and 0620. In order to check the loss of the plasmid pKD46, the strain GBE1353_pKD46 was plated on LB plates and incubated overnight at 42° C. The loss of the plasmid pKD46 was verified by plating isolated colonies on LB plates containing ampicilline (100 ug/ml), incubated overnight at 30° C., and on LB plates incubated overnight at 37° C. The resulting strain grew on LB plates incubated at 37° C. and was named GBE1353. GBE1353 cells did not grow on LB plates supplied with ampicilline (100 ug/ml).

The spectinomycin cassette was located at the corresponding loci of the zwf_edd_eda genes and the apramycin cassette was located at the corresponding loci of the pfkA genes. In order to excise the resistant cassettes containing the spectinomycin and apramycin resistance genes, the strain GBE1353 was transformed with the plasmid pCP20 to obtain the strain GBE1353_p. After overnight incubation on LB plates containing ampicilline (100 ug/ml) at 30° C., isolated colonies were restreaked on LB plates supplied with ampicilline (100 ug/ml) and incubated overnight at 30° C. Isolated colonies were then plated on LB plates and incubated overnight at 42° C. which caused the loss of the pCP20 plasmid. Then, in order to check the effective excision of the two resistant cassettes and the loss of the pCP20 plasmid, isolated colonies were streaked out on LB plates containing spectinomycin (50 ug/ml), incubated overnight at 37° C., on LB plates containing apramycin (50 ug/ml), incubated overnight at 37° C., on LB plates containing ampicilline (100 ug/ml), incubated overnight at 30° C. and on LB plates, incubated overnight at 37° C. The resulting strain grew on LB plates incubated at 37° C. and was named GBE1368. GBE1368 cells did not grow on LB plates containing spectinomycin (50 ug/ml), on LB plates containing apramycin (50 ug/ml), and on LB plates supplied with ampicilline (100 ug/ml).

Strain GBE1368 was made electrocompetent, and GBE1368 electrocompetent cells were transformed with plasmid pKD46. Transformant cells were then plated on LB plates containing ampicilline (100 ug/ml) and plates were incubated overnight at 30° C. to obtain a new strain named GBE1371. A PCR product was generated by using the plasmid pGBE0688 as a template and the oligonucleotides 0631 and 0632 (given as SEQ RC0011 and RC0012, respectively) as primers. The resulting 1.3 Kbp PCR product was transformed into electrocompetent GBE1371 bacteria and the transformation mixture was plated on LB plates containing spectinomycin (50 ug/ml). Plates were incubated overnight at 37° C. to generate strain GBE1420_pKD46. In Strain GBE1420_pKD46 the phosphofructokinase gene pfkB, was deleted and the deleted DNA sequence was replaced by a cassette containing the spectinomycin resistance gene. To check that the deletion of the pfkB gene occurred, a PCR amplification was performed with primers 0621 and 0622 (given as SEQ RC0013 and RC0014, respectively). This final 2.2 Kbp PCR product was sequenced by using the same primers 0621 and 0622.

In order to induce the loss of the plasmid pKD46, strain GBE1420_pKD46 was plated on LB plates and plates were incubated overnight at 42° C. The loss of the plasmid pKD46 was checked by plating isolated colonies on LB plates supplied with ampicilline (100 ug/ml), incubated overnight at 30° C., and on LB plates incubated overnight at 37° C. The resulting strain growing on LB plates incubated at 37° C. was named GBE1420. GBE1420 cells did not grow on LB plates supplied with ampicilline (100 ug/ml).

Example 15: Acetone Production by the Strains GBE2268 and GBE2269

Description of Plasmid Transformation into Relevant Strains

The strain GBE1283 was made electrocompetent, and GBE1283 electrocompetent cells were transformed with plasmid pGB1021. Transformants were then plated on LB plates containing ampicilline (100 ug/ml) and plates were incubated overnight at 30° C. to generate strain GBE2266.

Strain GBE1420 was made electrocompetent, and GBE1420 electrocompetent cells were transformed with the plasmid pGBE1020. Transformants were then plated on LB plates supplied with ampicilline (100 ug/ml). Plates were incubated overnight at 30° C. to obtain strain GBE2267.

Isolated colonies from strains GBE2266 and GBE2267 were screened on MS plates containing glucose as the source of carbon (2 g/L) and ampicilline (100 ug/ml). These plates were incubated at 30° C. to obtain strains GBE2268 and GBE2269 respectively. After 4 days of incubation at 30° C., colonies were transferred to MS liquid medium containing glucose (2 g/L), yeast extract (0.1 g/L) and ampicilline (100 ug/ml) and incubated 3 days at 30° C.

Description of Flasks Conditions

MSP liquid medium (200 ml) containing glucose (10 g/L), yeast extract (0.1 g/L) and ampicilline (100 ug/ml), were inoculated either with pre culture of strain GBE2268 or with pre culture of strain GBE2269. The initial $OD_{600}$ was 0.1. The 200 ml of culture was incubated in 250 ml bottles, sealed with a screw cap, at 30° C., 170 rpm of speed. Aliquots (2 ml) were taken after 1 day, 2 days, 4 days, 5 days, 6 days, 7 days and 8 days. For each aliquot sample, the bottle was open for 10 seconds.

Description of Analytical Methods

Aliquots were filtered and the glucose concentration was determined by HPLC analysis using the Agilent HPLC (1260 Infinity) and a Hi-Plex Colomn (Agilent, PL1170-6830) with a guard column (Agilent, PL Hi-Plex H Guard Column, PL1170-1830).

Volume of injection: 20 µl
Solvent composition: [$H_2SO_4$]: 5.5 mM
Temperature of the columns: 65° C.
RID (G1362A): temperature set: 35° C.

Acetone was extracted from the filtered aliquots by mixing with methyl acetate (1 volume of methyl acetate for 2 volumes of filtered aliquot). Acetone concentration was determined by gas chromatography using Gas chromatograph 450-GC (Bruker) and the following program:

Column: DB-WAX (123-7033, Agilent Technologies)
Injector:
  Split ratio: 10
  T°=250° C.
Oven:
  50° C. for 9 minutes
  20° C. per minute until 180° C.
  180° C. for 5 minutes
  Column flow: 1.5 ml/minute (Nitrogen)
Detector FID: T°=300° C.

Results

The ratio [acetone] produced (mM)/[glucose] consumed (mM) was higher for the strain GBE2269 than for the strain GBE2268.

Example 16: Acetone Production by the Strains GBE2272 and GBE2273

Description of Plasmid Transformation into Relevant Strains

The strain GBE2256 was made electrocompetent, and GBE2256 electrocompetent cells were transformed with plasmid pGB1020. Transformants were then plated on LB plates containing ampicilline (100 ug/ml) and plates were incubated overnight at 30° C. to generate strain GBE2270.

Strain GBE1518 was made electrocompetent, and GBE1518 electrocompetent cells were transformed with the plasmid pGBE1020. Transformants were then plated on LB plates supplied with ampicilline (100 ug/ml). Plates were incubated overnight at 30° C. to obtain strain GBE2271.

Isolated colonies from strains GBE2270 and GBE2271 were screened on MS plates containing glucose as the source of carbon (2 g/L) and ampicilline (100 ug/ml). These plates were incubated at 30° C. to obtain strains GBE2272 and GBE2273, respectively. After 4 days of incubation at 30° C., colonies were transferred to MS liquid medium containing glucose (2 g/L), yeast extract (0.1 g/L) and ampicilline (100 ug/ml) and incubated 3 days at 30° C.

Description of Flasks Conditions

MSP liquid medium (200 ml) containing glucose (10 g/L), yeast extract (0.1 g/L) and ampicilline (100 ug/ml), were inoculated either with pre culture of strain GBE2272 or with pre culture of strain GBE2273. The initial $OD_{600}$ was 0.1. The 200 ml of culture was incubated in 250 ml bottles, sealed with a screw cap, at 30° C., 170 rpm of speed. Aliquots (2 ml) were taken after 1 day, 2 days, 4 days, 5 days and 6 days. For each aliquot sample, the bottle was open for 10 seconds.

Description of Analytical Methods

Aliquots were filtered and the glucose concentration was determined by HPLC analysis using the Agilent HPLC (1260 Infinity) and a Hi-Plex Colomn (Agilent, PL1170-6830) with a guard column (Agilent, PL Hi-Plex H Guard Column, PL1170-1830).

Volume of injection: 20 μl
Solvent composition: [$H_2SO_4$]: 5.5 mM
Temperature of the columns: 65° C.
RID (G1362A): temperature set: 35° C.

Acetone was extracted from the filtered aliquots by mixing with methyl acetate (1 volume of methyl acetate for 2 volumes of filtered aliquot). Acetone concentration was determined by gas chromatography using Gas chromatograph 450-GC (Bruker) and the following program:

Column: DB-WAX (123-7033, Agilent Technologies)
Injector:
  Split ratio: 10
  T°. 250° C.
Oven:
  50° C. for 9 minutes
  20° C. per minute until 180° C.
  180° C. for 5 minutes
  Column flow: 1.5 ml/minute (Nitrogen)
Detector FID: T°=300° C.

Results

The ratio [acetone] produced (mM)/[glucose] consumed (mM) was higher for the strain GBE2273 than for the strain GBE2272.

---

The invention claimed is:

1. A recombinant microorganism characterized by:
   a) having phosphoketolase activity;
   b) (i) having a diminished or inactivated Embden-Meyerhof-Parnas pathway (EMPP) by inactivation of the gene(s) encoding phosphofructokinase or by being genetically modified so as to reduce phosphofructokinase activity as compared to a non-genetically modified microorganism; or
      (ii) not possessing phosphofructokinase activity; and
   c) (i) having a diminished or inactivated oxidative branch of the pentose phosphate pathway (PPP) by inactivation of the gene(s) encoding glucose-6-phosphate dehydrogenase or by being genetically modified so as to reduce glucose-6-phosphate dehydrogenase activity as compared to a non-genetically modified microorganism; or
      (ii) not possessing glucose-6-phosphate dehydrogenase activity; and
   d) furthermore characterized in that the activity of one or more of the enzymes selected from the group consisting of:
      formate C-acetyltransferase, classified as EC 2.3.1.54;
      acetate kinase, classified as EC 2.7.2.1
      L-lactate dehydrogenase, classified as EC 1.1.1.28
      phosphoenolpyruvate carboxylase, classified as EC 4.1.1.31
      phosphoenolpyruvate carboxykinase, classified as (ATP) EC 4.1.1.49
      succinate dehydrogenase, classified as EC 1.3.99.1
      pyruvate decarboxylase, classified as EC 4.1.1.1
      acetaldehyde dehydrogenase (acetylating), classified as EC 1.2.1.10
      glycerol-3-phosphate dehydrogenase [NAD(P)$^+$], classified as EC 1.1.94
      acetolactate synthase, classified as EC 2.2.1.6
      methylglyoxal synthase, classified as EC 4.2.3.3
      formate hydrogenlyase, classified as EC 1.2.1.2 together with EC 1.12.1.2
      is eliminated or reduced.

2. The recombinant microorganism of claim 1 further characterized by:
   d) having fructose-1,6-bisphosphate phosphatase activity.

3. The recombinant microorganism of claim 1, wherein the EMPP is further diminished or inactivated by inactivation of the gene(s) encoding glyceraldehyde 3-phosphate dehydrogenase or by being genetically modified so as to reduce glyceraldehyde 3-phosphate dehydrogenase activity as compared to a non-genetically modified microorganism.

4. The recombinant microorganism of claim 1 which has been genetically modified to have an increased phosphoketolase activity.

5. The recombinant microorganism of claim 1, wherein said microorganism is a fungus.

6. The recombinant microorganism of claim 1, wherein said microorganism is a bacterium.

7. The recombinant microorganism of claim 6, wherein the gene(s) encoding the PEP-dependent PTS transporter has/have been inactivated.

8. The recombinant microorganism of claim 1 further characterized in that it:
   e) is capable of converting acetyl-CoA into acetone.

9. The recombinant microorganism of claim 8 further characterized in that it:
   f) is capable of converting acetone into isobutene.

10. The recombinant microorganism of claim 8 further characterized in that it:
    g) is capable of converting acetone into propene.

11. Use of the recombinant microorganism of claim 1 for the conversion of glucose into acetyl-CoA.

12. Use of the recombinant microorganism of claim 8 for the conversion of glucose into acetone.

13. Use of the recombinant microorganism of claim 9 for the conversion of glucose into isobutene.

14. Use of the recombinant microorganism of claim 10 for the conversion of glucose into propene.

15. A method for producing acetone from glucose comprising the steps of:
    culturing the microorganism of claim 8 in a suitable medium; and
    optionally recovering said acetone from the culture medium.

16. A method for producing isobutene from glucose comprising the steps of:
    culturing the microorganism of claim 9 in a suitable medium; and
    optionally recovering said isobutene.

17. A method for producing propene from glucose comprising the steps of:
    culturing the microorganism of claim 10 in a suitable medium; and
    optionally recovering said propene.

18. The recombinant microorganism of claim 6, which is E. coli.

19. The recombinant microorganism of claim 8, wherein the fnr gene and/or the rpoS gene are deleted.

* * * * *

SEQUENCE LISTING

<160> NUMBER OF SEQ ID NOS: 54

<210> SEQ ID NO 1
<211> LENGTH: 134
<212> TYPE: DNA
<213> ORGANISM: Artificial Sequence
<220> FEATURE:
<223> OTHER INFORMATION: Synthetic

<400> SEQUENCE: 1

```
aggctagact ttagttccac aacactaaac ctataagttg gggaaataca gtgtaggctg      60
gagctgcttc gaagttccta tactttctag agaataggaa cttcggaata ggaactaagg     120
aggatattca tatg                                                       134
```

<210> SEQ ID NO 2
<211> LENGTH: 1205
<212> TYPE: DNA
<213> ORGANISM: Artificial Sequence
<220> FEATURE:
<223> OTHER INFORMATION: Synthetic

<400> SEQUENCE: 2

```
agagcggccg ccaccgcggg aagttcctat actttctaga gaataggaac ttcagctgat      60
agaaacagaa gccactggag cacctcaaaa acaccatcat acactaaatc agtaagttgg     120
cagcatcacc cgacgcactt tgcgccgaat aaatacctgt gacggaagat cacttcgcag     180
aataaataaa tcctggtgtc cctgttgata ccgggaagcc ctgggccaac ttttggcgaa     240
aatgagacgt tgatcggcac gtaagaggtt ccaactttca ccataatgaa ataagatcac     300
taccgggcgt attttttgag ttatcgagat tttcaggagc taaggaagct acatatgagt     360
gaaaaagtgc ccgccgagat tcggtgcaa ctatcacaag cactcaacgt catcgggcgc      420
cacttggagt cgacgttgct ggccgtgcat ttgtacggct ccgcactgga tggcggattg     480
aaaccgtaca gtgatattga tttgctggtg actgtagctg caccgctcaa tgatgccgtg     540
cggcaagccc tgctcgtcga tctcttggag gtttcagctt ccctggcca aaacaaggca     600 ctccgcgcct tggaagtgac catcgtcgtg cacagtgaca tcgtacccttg gcgttatccg     660 gccaggcggg aactgcagtt cggagagtgg cagcgcaaag acatccttgc gggcatcttc     720
gagcccgcca caaccgattc tgacttggcg attctgctaa caaaggcaaa gcaacatagc     780
```

| | |
|---|---|
| gtcgtcttgg caggttcagc agcgaaggat ctcttcagct cagtcccaga aagcgatcta | 840 |
| ttcaaggcac tggccgatac tctgaagcta tggaactcgc cgccagattg ggcgggcgat | 900 |
| gagcggaatg tagtgcttac tttgtctcgt atctggtaca ccgcagcaac cggcaagatc | 960 |
| gcgccaaagg atgttgctgc cacttgggca atggcacgct tgccagctca acatcagccc | 1020 |
| atcctgttga atgccaagcg ggcttatctt gggcaagaag aagattattt gcccgctcgt | 1080 |
| gcggatcagg tggcggcgct cattaaattc gtgaagtatg aagcagttaa actgcttggt | 1140 |
| gccagccaat aagaagttcc tatactttct agagaatagg aacttcgcat gcacgcagca | 1200 |
| tatgc | 1205 |

<210> SEQ ID NO 3
<211> LENGTH: 1129
<212> TYPE: DNA
<213> ORGANISM: Artificial Sequence
<220> FEATURE:
<223> OTHER INFORMATION: Synthetic

<400> SEQUENCE: 3

| | |
|---|---|
| agagcggccg ccaccgcggg aagttcctat actttctaga gaataggaac ttcgggttca | 60 |
| tgtgcagctc catcagcaaa aggggatgat aagtttatca ccaccgacta tttgcaacag | 120 |
| tgccgttgat cgtgctatga tcgactgatg tcatcagcgg tggagtgcaa tgtcgtgcaa | 180 |
| tacgaatggc gaaaagccga gctcatcggt cagcttctca accttggggt tacccccggc | 240 |
| ggtgtgctgc tggtccacag ctccttccgt agcgtccggc cctcgaaga tgggccactt | 300 |
| ggactgatcg aggccctgcg tgctgcgctg gtccgggag ggacgctcgt catgccctcg | 360 |
| tggtcaggtc tggacgacga gccgttcgat cctgccacgt cgcccgttac accggacctt | 420 |
| ggagttgtct ctgacacatt ctggcgcctg ccaaatgtaa agcgcagcgc ccatccattt | 480 |
| gcctttgcgg cagcggggcc acaggcagag cagatcatct ctgatccatt gcccctgcca | 540 |
| cctcactcgc ctgcaagccc ggtcgcccgt gtccatgaac tcgatgggca ggtacttctc | 600 |
| ctcggcgtgg gacacgatgc caacacgacg ctgcatcttg ccgagttgat ggcaaaggtt | 660 |
| ccctatgggg tgccgagaca ctgcaccatt cttcaggatg gcaagttggt acgcgtcgat | 720 |
| tatctcgaga tgaccactg ctgtgagcgc tttgccttgg cggacaggtg gctcaaggag | 780 |
| aagagccttc agaaggaagg tccagtcggt catgcctttg ctcggttgat ccgctcccgc | 840 |
| gacattgtgg cgacagccct gggtcaactg gccgagatc cgttgatctt cctgcatccg | 900 |
| ccagaggcgg gatgcgaaga atgcgatgcc gctcgccagt cgattggctg agctcatgag | 960 |
| cggagaacga gatgacgttg gaggggcaag gtcgcgctga ttgctggggc aacacgtgga | 1020 |
| gcggatcggg gattgtcttt cttcagctcg ctgatgatat gctgacgctc aatgccgaag | 1080 |
| ttcctatact ttctagagaa taggaacttc gcatgcacgc agcatatgc | 1129 |

<210> SEQ ID NO 4
<211> LENGTH: 99
<212> TYPE: DNA
<213> ORGANISM: Artificial Sequence
<220> FEATURE:
<223> OTHER INFORMATION: Synthetic

<400> SEQUENCE: 4

| | |
|---|---|
| aagcttgcgg ccgcggggtt aattaacctc cttagtttaa acctaggcat gcctctagag | 60 |
| gatccccggg taccgagctc gaattacctg caggaattc | 99 |

<210> SEQ ID NO 5
<211> LENGTH: 2508
<212> TYPE: DNA
<213> ORGANISM: Artificial Sequence
<220> FEATURE:
<223> OTHER INFORMATION: Synthetic

<400> SEQUENCE: 5

| | | | | | |
|---|---|---|---|---|---|
| ttaattaatg | catcatcacc | accatcacat | gaccgaatat | aacagcgaag | cctatctgaa | 60 |
| aaaactggat | aaatggtggc | gtgcagcaac | ctatctgggt | gcaggtatga | tttttctgaa | 120 |
| agaaaatccg | ctgtttagcg | ttaccggcac | cccgattaaa | gcagaaaatc | tgaaagccaa | 180 |
| tccgattggt | cattggggca | ccgttagcgg | tcagaccttt | ctgtatgcac | atgcaaatcg | 240 |
| cctgattaac | aaatataacc | agaaaatgtt | ttatatgggt | ggtccgggtc | atggtggtca | 300 |
| ggcaatggtt | gttccgagct | atctggatgg | tagctatacc | gaagcatatc | cggaaattac | 360 |
| ccaggatctg | gaaggtatga | ccgtctgtt | taaacgtttt | agctttccgg | tggtattgg | 420 |
| tagccacatg | accgcacaga | caccgggtag | cctgcatgaa | ggtggtgaac | tgggttatgt | 480 |
| tctgagccat | gcaaccggtg | caattctgga | tcagccggaa | caaattgcat | ttgcagttgt | 540 |
| tggtgatggt | gaagcagaaa | ccggtccgct | gatgaccagc | tggcatagca | tcaaatttat | 600 |
| caacccgaaa | aacgatggtg | ccattctgcc | gattctggat | ctgaatggct | taaaatcag | 660 |
| caatccgacc | ctgtttgcac | gtaccagtga | tgttgatatc | cgcaaatttt | tcgaaggtct | 720 |
| gggttatagt | ccgcgttata | ttgaaaacga | tgacatccat | gactacatgg | cctatcataa | 780 |
| actggcagca | gaagttttg | acaaagccat | gaagatatc | catcgattc | agaaagatgc | 840 |
| ccgtgaagat | aatcgctatc | agaatggtga | aattccggca | tggccgattg | ttattgcacg | 900 |
| tctgccgaaa | ggttgggtg | gtcctcgtta | taatgattgg | agcggtccga | aatttgatgg | 960 |
| taaaggtatg | ccgatcgaac | atagctttcg | tgcacatcag | gttccgctgc | cgctgagcag | 1020 |
| caaaaacatg | gcacccctgc | cggaatttgt | taaatggatg | accagctatc | agccggaaac | 1080 |
| cctgtttaat | gcagatggta | gcctgaaaga | agaactgcgc | gattttgcac | gaaaggtga | 1140 |
| aatgcgtatg | gcaagcaatc | cggttaccaa | tggtggtgtt | gattatagca | atctggttct | 1200 |
| gccggattgg | caagaatttg | caaatccgat | tagcgaaaac | aatcgtggta | aactgctgcc | 1260 |
| ggataccaat | gataatatgg | atatgaacgt | gctgagcaaa | tatttcgccg | aaattgttaa | 1320 |
| actgaacccg | acccgttttc | gtctgtttgg | tccggatgaa | accatgagca | atcgttttg | 1380 |
| ggagatgttt | aaagtgacca | atcgtcagtg | gatgcaggtt | atcaaaaatc | cgaacgatga | 1440 |
| gtttattagt | ccggaaggtc | gcattattga | tagccagctg | agcgaacatc | aggcagaagg | 1500 |
| ttggctggaa | ggttataccc | tgaccggtcg | taccggtgtt | tttgcaagct | atgaaagttt | 1560 |
| tctgcgtgtt | gttgatagca | tgctgaccca | gcactttaaa | tggattcgtc | aggcagcaga | 1620 |
| tcagaaatgg | cgtcatgatt | atccgagcct | gaatgttatt | agcaccagca | ccgttttca | 1680 |
| gcaggatcat | aatggttata | cccatcaaga | tccgggtatg | ctgacccatc | tggcagagaa | 1740 |
| aaaaagcgat | tttattcgtc | agtatctgcc | tgcagatggt | aatacccctgc | tggccgtttt | 1800 |
| tgatcgtgca | tttcaggatc | gcagcaaaat | taaccatatt | gttgcaagca | aacagcctcg | 1860 |
| tcagcagtgg | tttaccaaag | aagaagcaga | aaaactggcc | accgatggta | ttgcaaccat | 1920 |
| tgattgggca | agcaccgcaa | aagatggtga | agccgttgat | ctggttttg | caagtgccgg | 1980 |
| tgcagaaccg | accattgaaa | ccctggcagc | actgcatctg | gttaatgaag | tttttccgca | 2040 |
| ggccaaattt | cgctatgtta | atgttgttga | actgggtcgt | ctgcagaaaa | agaaaggtgc | 2100 |

-continued

```
actgaatcaa gaacgcgaac tgagtgatga agagttcgaa aaatactttg gtccgagcgg    2160
tacaccggtt attttggtt ttcatggcta tgaagatctg atcgagagca tcttttatca     2220
gcgtggtcat gatggtctga ttgttcatgg ttatcgtgaa gatggtgata ttaccaccac    2280
ctatgatatg cgtgtttata gcgaactgga tcgttttcat caggcaattg atgcaatgca   2340
ggttctgtat gtgaatcgta aagttaatca gggtctggcc aaagcattta ttgatcgtat    2400
ggaacgtacc ctggtgaaac attttgaagt tacccgtaat gaaggcgttg atattccgga    2460
atttaccgaa tgggtttgga gcgatctgaa aaagtaatga gcggccgc                 2508
```

<210> SEQ ID NO 6
<211> LENGTH: 86
<212> TYPE: DNA
<213> ORGANISM: Artificial Sequence
<220> FEATURE:
<223> OTHER INFORMATION: Synthetic

<400> SEQUENCE: 6

```
gaattcgagc tcggtacccg gggatcctct agaggcatgc ctaggtttaa actaaggagg    60
ttaattaacc ccgcggccgc aagctt                                          86
```

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7

```
ggttcaattc ttcctttagc ggc                                             23
```

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8

```
ccgcaaaaac gacatccggc acg                                             23
```

<210> SEQ ID NO 9
<211> LENGTH: 70
<212> TYPE: DNA
<213> ORGANISM: Artificial Sequence
<220> FEATURE:
<223> OTHER INFORMATION: Synthetic

<400> SEQUENCE: 9

```
caagtatacc ctggcttaag taccgggtta gttaacttaa ggagaatgac agagcggccg    60
ccaccgcggg                                                            70
```

<210> SEQ ID NO 10
<211> LENGTH: 70
<212> TYPE: DNA
<213> ORGANISM: Artificial Sequence
<220> FEATURE:
<223> OTHER INFORMATION: Synthetic

<400> SEQUENCE: 10

```
gcaaaaaaac gctacaaaaa tgcccgatcc tcgatcgggc attttgactt gcatatgctg    60
```

```
cgtgcatgcg                                                             70

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
ccgcactttg cgcgcttttc cc                                               22

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
ggtgattttc agtgaggtct cccc                                             24

<210> SEQ ID NO 13
<211> LENGTH: 70
<212> TYPE: DNA
<213> ORGANISM: Artificial Sequence
<220> FEATURE:
<223> OTHER INFORMATION: Synthetic

<400> SEQUENCE: 13
agacttccgg caacagattt cattttgcat tccaaagttc agaggtagtc agagcggccg      60
ccaccgcggg                                                             70

<210> SEQ ID NO 14
<211> LENGTH: 70
<212> TYPE: DNA
<213> ORGANISM: Artificial Sequence
<220> FEATURE:
<223> OTHER INFORMATION: Synthetic

<400> SEQUENCE: 14
gcttctgtca tcggtttcag ggtaaaggaa tctgcctttt tccgaaatca gcatatgctg      60
cgtgcatgcg                                                             70

<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15
ggcgctcacg atcttcgcac gcggc                                            25

<210> SEQ ID NO 16
<211> LENGTH: 27
<212> TYPE: DNA
<213> ORGANISM: Artificial Sequence
<220> FEATURE:
<223> OTHER INFORMATION: Synthetic

<400> SEQUENCE: 16
ccgcctcata ttgctgacaa agtgcgc                                          27
```

-continued

```
<210> SEQ ID NO 17
<211> LENGTH: 70
<212> TYPE: DNA
<213> ORGANISM: Artificial Sequence
<220> FEATURE:
<223> OTHER INFORMATION: Synthetic

<400> SEQUENCE: 17
actttccgct gattcggtgc cagactgaaa tcagcctata ggaggaaatg agagcggccg    60
ccaccgcggg                                                          70

<210> SEQ ID NO 18
<211> LENGTH: 70
<212> TYPE: DNA
<213> ORGANISM: Artificial Sequence
<220> FEATURE:
<223> OTHER INFORMATION: Synthetic

<400> SEQUENCE: 18
gttgccgaca ggttggtgat gattccccca atgctggggg aatgttttg gcatatgctg    60 cgtgcatgcg                                                          70

<210> SEQ ID NO 19
<211> LENGTH: 27
<212> TYPE: DNA
<213> ORGANISM: Artificial Sequence
<220> FEATURE:
<223> OTHER INFORMATION: Synthetic

<400> SEQUENCE: 19
ccacagcgac caggcagtgg tgtgtcc                                       27

<210> SEQ ID NO 20
<211> LENGTH: 24
<212> TYPE: DNA
<213> ORGANISM: Artificial Sequence
<220> FEATURE:
<223> OTHER INFORMATION: Synthetic

<400> SEQUENCE: 20
gcactttggg taagccccga aacc                                          24

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
ccattcaggc tgcgcaactg                                               20

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
gcgcgttggc cgattcatta atgc                                          24

<210> SEQ ID NO 23
<211> LENGTH: 24
<212> TYPE: DNA
```

<213> ORGANISM: Artificial Sequence
<220> FEATURE:
<223> OTHER INFORMATION: Synthetic

<400> SEQUENCE: 23
caatccgacc ctgtttgcac gtac					24

<210> SEQ ID NO 24
<211> LENGTH: 26
<212> TYPE: DNA
<213> ORGANISM: Artificial Sequence
<220> FEATURE:
<223> OTHER INFORMATION: Synthetic

<400> SEQUENCE: 24
gctgccggat accaatgata atatgg					26

<210> SEQ ID NO 25
<211> LENGTH: 26
<212> TYPE: DNA
<213> ORGANISM: Artificial Sequence
<220> FEATURE:
<223> OTHER INFORMATION: Synthetic

<400> SEQUENCE: 25
ccatattatc attggtatcc ggcagc					26

<210> SEQ ID NO 26
<211> LENGTH: 32
<212> TYPE: DNA
<213> ORGANISM: Artificial Sequence
<220> FEATURE:
<223> OTHER INFORMATION: Synthetic

<400> SEQUENCE: 26
cccgggggat ccagaattta aaaggaggga tt					32

<210> SEQ ID NO 27
<211> LENGTH: 40
<212> TYPE: DNA
<213> ORGANISM: Artificial Sequence
<220> FEATURE:
<223> OTHER INFORMATION: Synthetic

<400> SEQUENCE: 27
ctcgaggata tcaagaattc tttttaaaca gccatgggtc					40

<210> SEQ ID NO 28
<211> LENGTH: 18
<212> TYPE: DNA
<213> ORGANISM: Artificial Sequence
<220> FEATURE:
<223> OTHER INFORMATION: Synthetic

<400> SEQUENCE: 28
tgtaaaacga cggccagt					18

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29
caggaaacag ctatgacc					18

<210> SEQ ID NO 30
<211> LENGTH: 37
<212> TYPE: DNA
<213> ORGANISM: Artificial Sequence
<220> FEATURE:
<223> OTHER INFORMATION: Synthetic

<400> SEQUENCE: 30
ctcgaggata tcaggaaggt gactttatg ttaaagg                                37

<210> SEQ ID NO 31
<211> LENGTH: 33
<212> TYPE: DNA
<213> ORGANISM: Artificial Sequence
<220> FEATURE:
<223> OTHER INFORMATION: Synthetic

<400> SEQUENCE: 31
gcatgcgtcg acattaaaaa aataagagtt acc                                   33

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
cctcacggca aagtctcaag c                                                21

<210> SEQ ID NO 33
<211> LENGTH: 22
<212> TYPE: DNA
<213> ORGANISM: Artificial Sequence
<220> FEATURE:
<223> OTHER INFORMATION: Synthetic

<400> SEQUENCE: 33
gccatgggtc taagttcatt gg                                               22

<210> SEQ ID NO 34
<211> LENGTH: 37
<212> TYPE: DNA
<213> ORGANISM: Artificial Sequence
<220> FEATURE:
<223> OTHER INFORMATION: Synthetic

<400> SEQUENCE: 34
catgatttta aggggggtac catatgcata agtttaa                               37

<210> SEQ ID NO 35
<211> LENGTH: 36
<212> TYPE: DNA
<213> ORGANISM: Artificial Sequence
<220> FEATURE:
<223> OTHER INFORMATION: Synthetic

<400> SEQUENCE: 35
gttattttta aggatccttt ttagcacttt tctagc                                36

<210> SEQ ID NO 36
<211> LENGTH: 22
<212> TYPE: DNA
<213> ORGANISM: Artificial Sequence
<220> FEATURE:

<223> OTHER INFORMATION: Synthetic

<400> SEQUENCE: 36
ggcagaaagg gagaaactgt ag                                       22

<210> SEQ ID NO 37
<211> LENGTH: 22
<212> TYPE: DNA
<213> ORGANISM: Artificial Sequence
<220> FEATURE:
<223> OTHER INFORMATION: Synthetic

<400> SEQUENCE: 37
tggaaagaat acgtgcaggc gg                                       22

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
gattacgcca agcttgcatg cc                                       22

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
ccggcctcat ctacaatact acc                                      23

<210> SEQ ID NO 40
<211> LENGTH: 23
<212> TYPE: DNA
<213> ORGANISM: Artificial Sequence
<220> FEATURE:
<223> OTHER INFORMATION: Synthetic

<400> SEQUENCE: 40
cccattattg ctgggtcaac tcc                                      23

<210> SEQ ID NO 41
<211> LENGTH: 38
<212> TYPE: DNA
<213> ORGANISM: Artificial Sequence
<220> FEATURE:
<223> OTHER INFORMATION: Synthetic

<400> SEQUENCE: 41
cccggtacct cattactttt tcagatcgct ccaaaccc                      38

<210> SEQ ID NO 42
<211> LENGTH: 50
<212> TYPE: DNA
<213> ORGANISM: Artificial Sequence
<220> FEATURE:
<223> OTHER INFORMATION: Synthetic

<400> SEQUENCE: 42
ggggaattca ggaggtgtac tagatgcatc atcaccacca tcacatgacc         50

<210> SEQ ID NO 43
<211> LENGTH: 26
<212> TYPE: DNA
<213> ORGANISM: Artificial Sequence
<220> FEATURE:
<223> OTHER INFORMATION: Synthetic

<400> SEQUENCE: 43
ccatagctcc acccatacca gagagc                                              26

<210> SEQ ID NO 44
<211> LENGTH: 26
<212> TYPE: DNA
<213> ORGANISM: Artificial Sequence
<220> FEATURE:
<223> OTHER INFORMATION: Synthetic

<400> SEQUENCE: 44
gctattatta cgtcagcatc tcctgc                                              26

<210> SEQ ID NO 45
<211> LENGTH: 22
<212> TYPE: DNA
<213> ORGANISM: Artificial Sequence
<220> FEATURE:
<223> OTHER INFORMATION: Synthetic

<400> SEQUENCE: 45
gcaggcgaag ttaatggcgt gc                                                  22

<210> SEQ ID NO 46
<211> LENGTH: 27
<212> TYPE: DNA
<213> ORGANISM: Artificial Sequence
<220> FEATURE:
<223> OTHER INFORMATION: Synthetic

<400> SEQUENCE: 46
gatacggggt aacagataaa ccatttc                                             27

<210> SEQ ID NO 47
<211> LENGTH: 26
<212> TYPE: DNA
<213> ORGANISM: Artificial Sequence
<220> FEATURE:
<223> OTHER INFORMATION: Synthetic

<400> SEQUENCE: 47
ccctttctgc ctttaattac tacagg                                              26

<210> SEQ ID NO 48
<211> LENGTH: 26
<212> TYPE: DNA
<213> ORGANISM: Artificial Sequence
<220> FEATURE:
<223> OTHER INFORMATION: Synthetic

<400> SEQUENCE: 48
gcatcaggat taaatgactg tgcagc                                              26

<210> SEQ ID NO 49
<211> LENGTH: 26
<212> TYPE: DNA
<213> ORGANISM: Artificial Sequence
<220> FEATURE:
<223> OTHER INFORMATION: Synthetic

```
<400> SEQUENCE: 49
ggactagcgc ccattccaac tattcc                                          26

<210> SEQ ID NO 50
<211> LENGTH: 29
<212> TYPE: DNA
<213> ORGANISM: Artificial Sequence
<220> FEATURE:
<223> OTHER INFORMATION: Synthetic

<400> SEQUENCE: 50
gctgcaaggc gattaagttg ggtaacgcc                                       29

<210> SEQ ID NO 51
<211> LENGTH: 25
<212> TYPE: DNA
<213> ORGANISM: Artificial Sequence
<220> FEATURE:
<223> OTHER INFORMATION: Synthetic

<400> SEQUENCE: 51
gcattgcgtg tacaagagta acgag                                           25

<210> SEQ ID NO 52
<211> LENGTH: 22
<212> TYPE: DNA
<213> ORGANISM: Artificial Sequence
<220> FEATURE:
<223> OTHER INFORMATION: Synthetic

<400> SEQUENCE: 52
cctgtccaag cttcatgtac gg                                              22

<210> SEQ ID NO 53
<211> LENGTH: 70
<212> TYPE: DNA
<213> ORGANISM: Artificial Sequence
<220> FEATURE:
<223> OTHER INFORMATION: Synthetic

<400> SEQUENCE: 53
gcgcaagatc atgttaccgg taaaataacc ataaaggata agcgcagata gcatatgctg     60
cgtgcatgcg                                                            70

<210> SEQ ID NO 54
<211> LENGTH: 24
<212> TYPE: DNA
<213> ORGANISM: Artificial Sequence
<220> FEATURE:
<223> OTHER INFORMATION: Synthetic

<400> SEQUENCE: 54
cgcctgtaac cggagctcat aggg                                            24
```